US008891087B2

(12) United States Patent
Zuzak et al.

(10) Patent No.: US 8,891,087 B2
(45) Date of Patent: Nov. 18, 2014

(54) SYSTEM AND METHOD FOR HYPERSPECTRAL IMAGING

(75) Inventors: Karel J. Zuzak, Arlington, TX (US); William Boyd Werner, Austin, TX (US); Duane Scott Dewald, Dallas, TX (US); Brian Crowell, Austin, TX (US)

(73) Assignee: Digital Light Innovations, Austin, TX (US)

( * ) Notice: Subject to any disclaimer, the term of this patent is extended or adjusted under 35 U.S.C. 154(b) by 165 days.

(21) Appl. No.: 13/492,753

(22) Filed: Jun. 8, 2012

(65) Prior Publication Data

US 2012/0307056 A1 Dec. 6, 2012

Related U.S. Application Data

(63) Continuation-in-part of application No. 13/487,127, filed on Jun. 1, 2012.

(60) Provisional application No. 61/492,139, filed on Jun. 1, 2011, provisional application No. 61/494,717, filed on Jun. 8, 2011.

(51) Int. Cl.
*G01N 21/55* (2014.01)
*G01N 21/31* (2006.01)
*G01N 21/64* (2006.01)
*G02B 21/06* (2006.01)
*G01N 21/21* (2006.01)

(52) U.S. Cl.
CPC .... G01N 21/6456 (2013.01); *G01N 2021/6423* (2013.01); *G02B 21/06* (2013.01); G01N 21/31 (2013.01); *G01N 2021/216* (2013.01); *G01N 2021/3144* (2013.01); *G01N 2201/1293* (2013.01); *G01N 21/21* (2013.01)
USPC ........................................................... 356/445

(58) Field of Classification Search
CPC ................. G06K 9/00; G01J 3/00; G01J 3/40
USPC ........................... 356/300, 303, 445; 382/128
See application file for complete search history.

(56) References Cited

U.S. PATENT DOCUMENTS

| | | | |
|---|---|---|---|
| 5,029,245 A * | 7/1991 | Keranen et al. | 250/205 |
| 5,372,135 A | 12/1994 | Mendelson et al. | |
| 6,142,629 A * | 11/2000 | Adel et al. | 351/206 |
| 6,198,532 B1 * | 3/2001 | Cabib et al. | 356/456 |
| 7,060,955 B1 * | 6/2006 | Wang | 250/205 |
| 7,218,656 B2 * | 5/2007 | Nishimura | 372/38.02 |
| 7,219,086 B2 | 5/2007 | Geshwind et al. | |
| 7,321,791 B2 * | 1/2008 | Levenson et al. | 600/476 |
| 7,529,004 B2 * | 5/2009 | Debevec et al. | 358/509 |
| 7,573,575 B2 * | 8/2009 | Shakespeare et al. | 356/402 |

(Continued)

OTHER PUBLICATIONS

International Search Report and Written Opinion date mailed Oct. 17, 2012; PCT International Patent Application No. PCT/US2012/040612.

(Continued)

*Primary Examiner* — Roy M Punnoose
(74) *Attorney, Agent, or Firm* — Simpson & Simpson, PLLC

(57) ABSTRACT

A system and method for visualizing a biological sample. One or more spectra are selected for illuminating the biological sample to indicate one or more chemicals in the biological sample. The biological sample is illuminated with the one or more spectra. Reflected light is analyzed to determine characteristics of the biological sample.

23 Claims, 23 Drawing Sheets

(56) References Cited

U.S. PATENT DOCUMENTS

| | | |
|---|---|---|
| 7,586,674 B2 | 9/2009 | O'Connell |
| 7,852,553 B2 | 12/2010 | Tsutsui et al. |
| 8,385,615 B2 * | 2/2013 | Levenson et al. .............. 382/128 |
| 8,391,961 B2 * | 3/2013 | Levenson et al. .............. 600/476 |
| 8,406,859 B2 * | 3/2013 | Zuzak et al. ................... 600/476 |
| 8,634,607 B2 * | 1/2014 | Levenson et al. .............. 382/128 |
| 2001/0052978 A1 * | 12/2001 | Lewis et al. ................... 356/326 |
| 2002/0001080 A1 | 1/2002 | Miller et al. |
| 2004/0188594 A1 * | 9/2004 | Brown et al. ................. 250/205 |
| 2006/0241495 A1 | 10/2006 | Kurtz |
| 2007/0024946 A1 | 2/2007 | Panasyuk et al. |
| 2007/0249913 A1 * | 10/2007 | Freeman et al. .............. 600/300 |
| 2007/0290145 A1 | 12/2007 | Viellerobe et al. |
| 2008/0065176 A1 | 3/2008 | Zhang et al. |
| 2008/0213915 A1 | 9/2008 | Durack et al. |
| 2009/0051926 A1 | 2/2009 | Chen |
| 2010/0277580 A1 | 11/2010 | Stallinga et al. |
| 2011/0068279 A1 | 3/2011 | Fay |

OTHER PUBLICATIONS

Kliner, et al., Development of Fiber-Laser-Based Laser-Induced Fluorescence for Detection of $SO_2$, Dec. 1998 [retrieved on Sep. 27, 2012]. Retrieved from the Internet: URL:http://www.osti.gov/bridge/servlets/purl/751016-jyJOwN/webviewable/751016.pdf p. 7, para [0003].

International Search Report and Written Opinion date mailed Aug. 7, 2012; PCT International Patent Application No. PCT/US2012/041767.

* cited by examiner

FIG. 20A
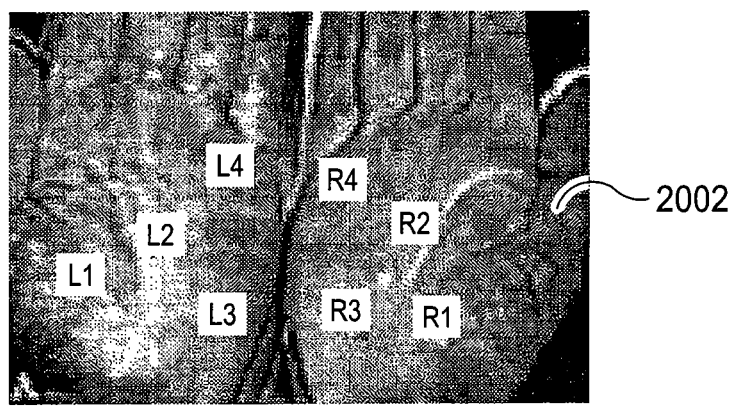
FIG. 20B
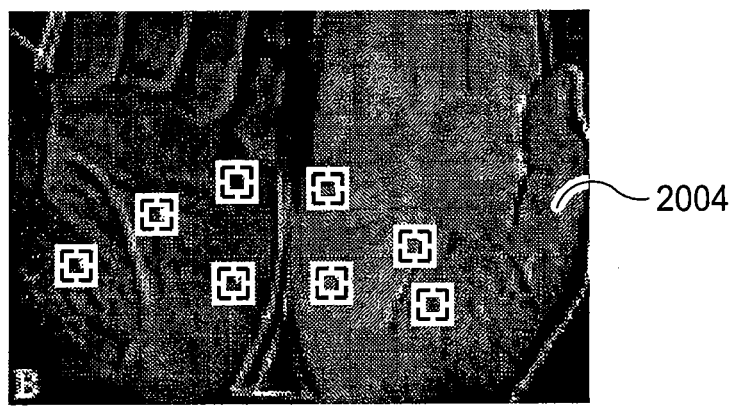
FIG. 20C
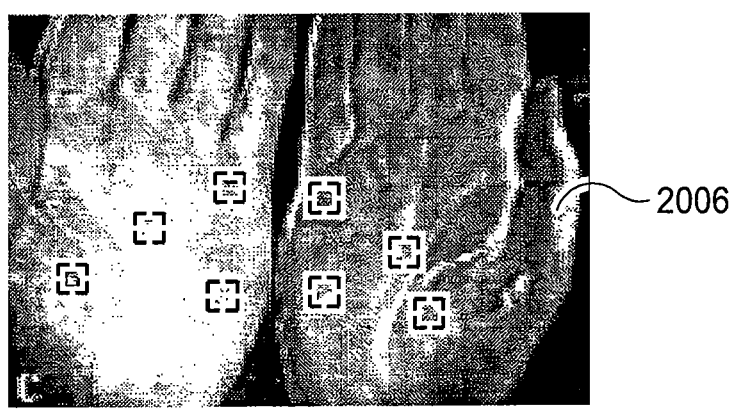
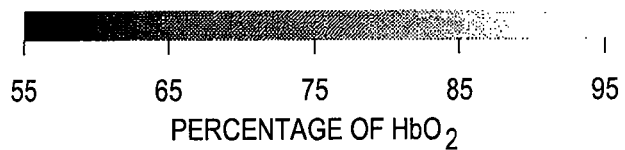
PERCENTAGE OF $HbO_2$

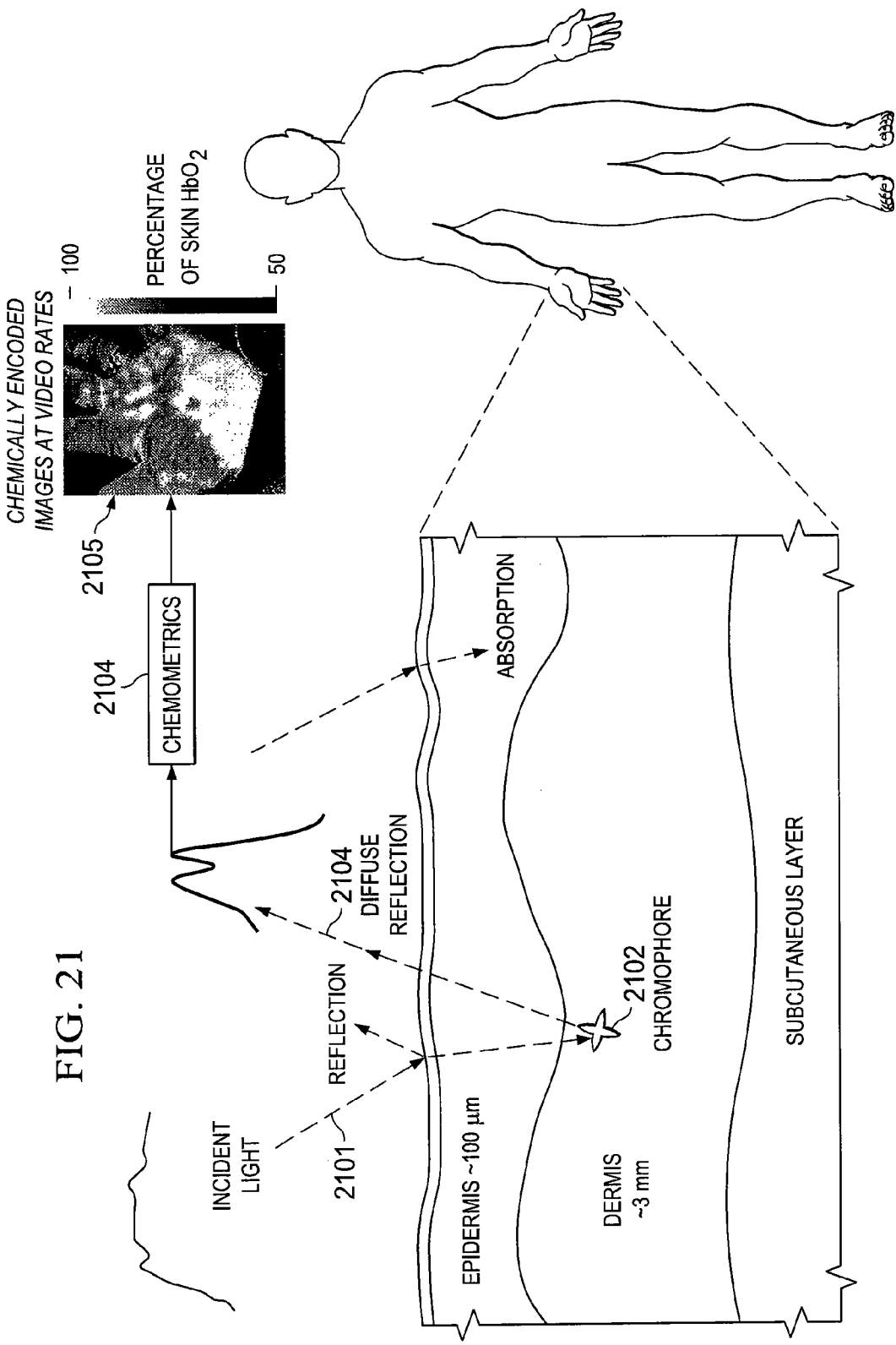

SYSTEM AND METHOD FOR HYPERSPECTRAL IMAGING

CROSS REFERENCE TO RELATED APPLICATIONS

This Application claims priority from the following U.S. Provisional Patent Application 61/494,717 filed Jun. 8, 2011 and is a Continuation-In-Part of U.S. patent application Ser. No. 13/487,127 filed on Jun. 1, 2012 entitled SYSTEM AND METHOD FOR HYPERSPECTRAL ILLUMINATION which claims priority from the following U.S. Provisional Patent Applications Ser. No. 61/492,139 filed Jun. 1, 2011, and 61/494,717 filed Jun. 8, 2011; the entire teachings of which are incorporated herein by reference.

BACKGROUND

Hyperspectral imaging involves collecting and processing information from across the electromagnetic spectrum. Just as the human eye can process visible light within a rainbow of colors consisting of red, green, and blue hues, spectral imaging divides the spectrum into many more bands (including non-visible light) for processing. In recent years, scientists, doctors, and companies have begun to image/visualize organic (biochemical) materials, such as skin to predict, detect, monitor, and assess skin and other wounds. Diagnosing, monitoring and predicting the severity and assessing risk of potential disease or medical conditions may be complicated and difficult. For example, determining the severity and depth of a wound may be difficult using existing processes. In addition, existing hyperspectral imaging systems are large, expensive, provide insufficient output, and are inefficient.

SUMMARY

One embodiment includes a system, method, and imaging system for visualizing a biological sample. One or more spectra may be selected for illuminating the biological sample to indicate one or more chemicals in the biological sample. The biological sample may be illuminated with the one or more color spectra. Reflected light may be analyzed to determine characteristics of the biological sample.

Another embodiment provides an imaging system. The imaging system may include a hyperspectral illuminator configured to illuminate a target utilizing multiple spectra. The imaging system may further include a camera in communication with the hyperspectral illuminator and configured to capture one or more images for each of the multiple spectra. The imaging system may also include a data processing system controlling the hyperspectral illuminator and the camera. The data processing system may process data captured by the camera. The data processing system may trigger illumination of the target for each of the multiple spectra. The data processing system may control exposure of the camera for each of the multiple spectra.

Yet another embodiment provides a method for performing image. A target may be illuminated with multiple spectra. An image sensor of an imaging system may be exposed for one of multiple time periods associated with each of the multiple spectra. Reflectance images from the target may be processed utilizing chemometric algorithms. One or more chemicals may be visualized in the target.

BRIEF DESCRIPTION OF THE DRAWINGS

Illustrative embodiments of the present invention are described in detail below with reference to the attached drawing figures, which are incorporated by reference herein and wherein:

FIGS. 19-20 show illustrative images of hyperspectral imaging in accordance with illustrative embodiments;

FIG. 21 is a pictorial representation of hyperspectral imaging in accordance with an illustrative embodiment;

DETAILED DESCRIPTION OF THE DRAWINGS

The illustrative embodiments provide a system and method for hyperspectral illumination including a hyperspectral illuminator and system and method for hyperspectral illumination. In one embodiment, the systems and methods described may be utilized to analyze an object, such as biological tissue and samples (i.e. human, animal, etc). Light absorption, reflection, contrast, and other interactions of light with the object may be analyzed by an imaging device, such as a video camera to perform analysis of the tissue. In particular, the light-absorbing or characteristics of the tissue may be analyzed to distinguish between different tissues types (i.e. healthy, diseased, stained, damaged tissue, etc).

Figure 1:
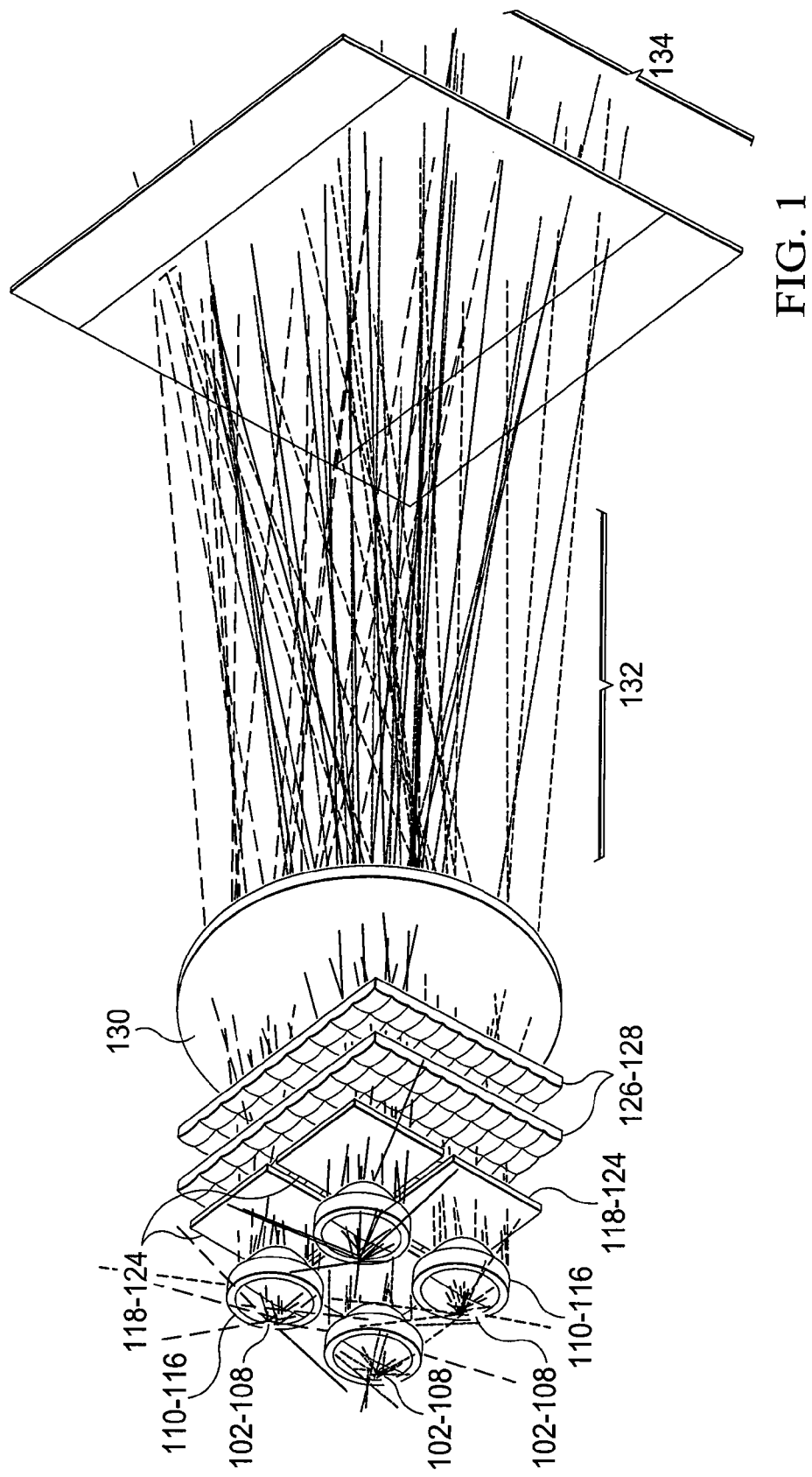
FIGS. 1-3 are a pictorial representation of a hyperspectral illuminator in accordance with an illustrative embodiment.
Figure 2:
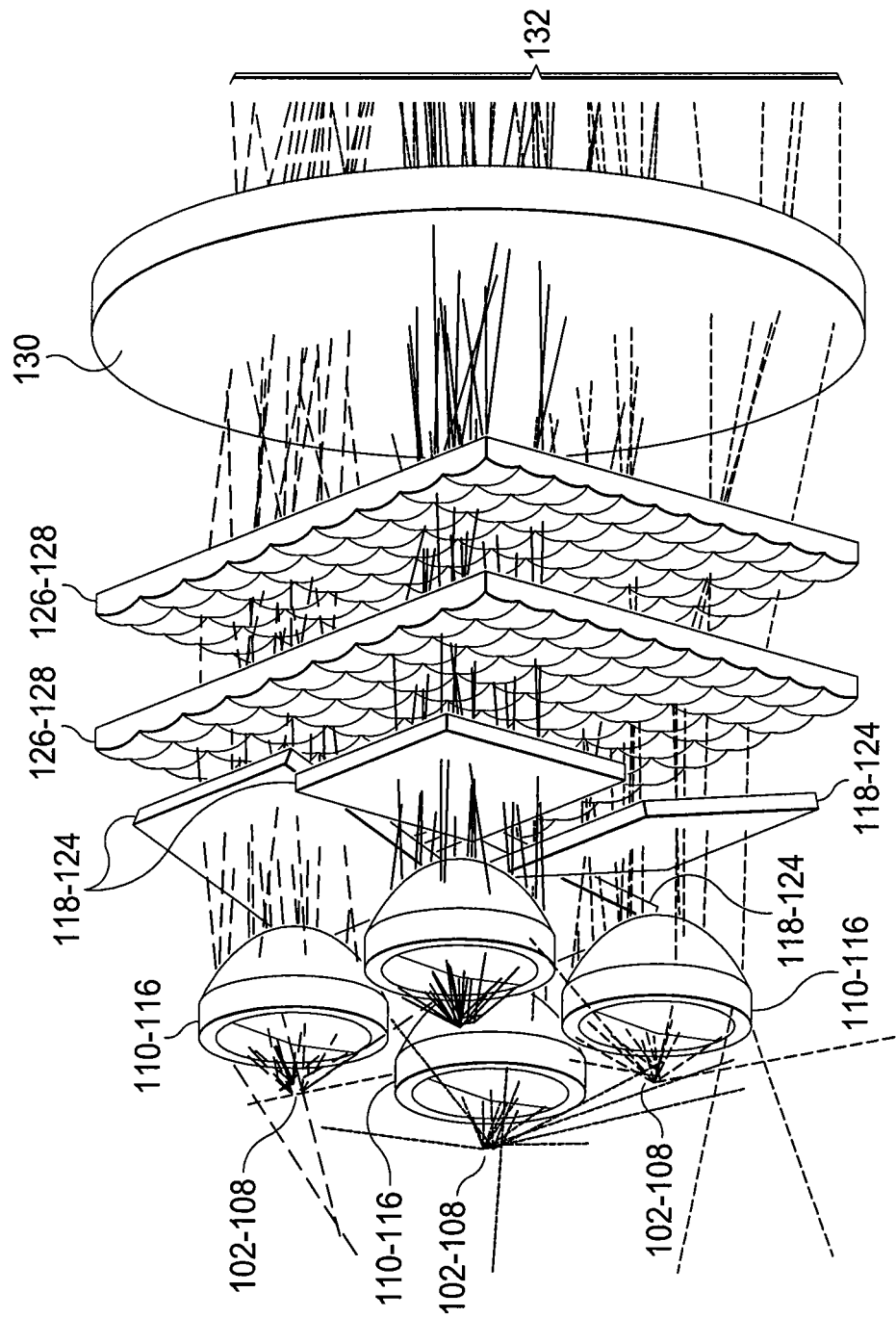
Figure 3:
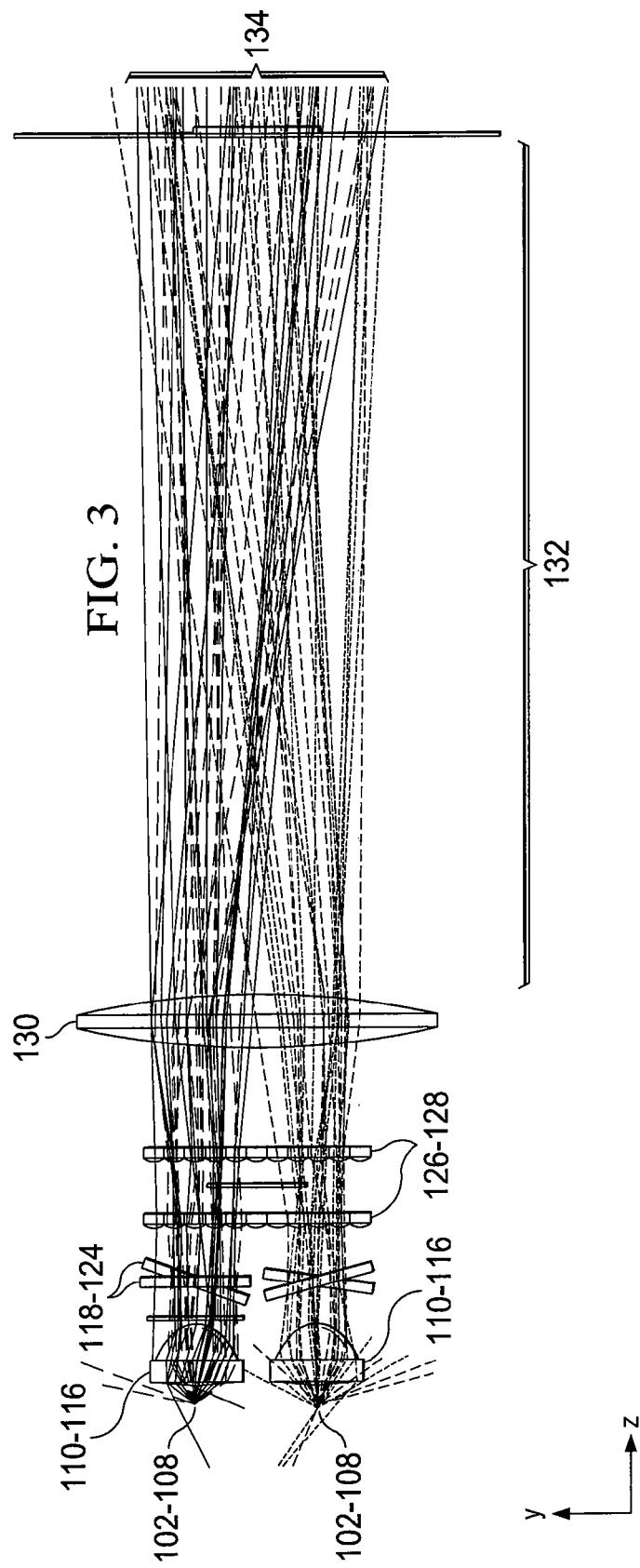

FIGS. 1-3 are pictorial representations of a hyperspectral illuminator 100 in accordance with an illustrative embodiment. FIG. 1 illustrates portions of the hyperspectral illuminator 100. The hyperspectral illuminator 100 may utilized with an imaging system to perform hyperspectral imaging across a number of spectra. In one embodiment, the hyperspectral illuminator 100 may include LEDs 102, 104, 106, and 108, collimators 110, 112, 114, and 116, dichroic filters 118, 120, 122, and 124, integrator lenses 126 and 128, focus lens 130, illumination 132, illumination field 134, object 136. The components of FIG. 1 may describe illumination optics of a system. The overall system may include an illumination module including the illumination optics as well as an imaging, control, process, and data output module and/or components. A hyperspectral imaging system (i.e. the hyperspectral illuminator 100, focal plane array detector, and managing software and chemometrics, such as those shown in FIG. 14) may be integrated with other systems, such as robotic systems, endoscopes, and surgical microscopes.

The LEDs 102, 104, 106, and 108 may generate light at different colors and frequencies. In one embodiment, the LEDs 102, 104, 106, and 108 may be an LED array. The LED array may include potentially hundreds or thousands of LEDs. For example, a larger LED array (e.g. FIG. 4) along with an imaging system and managing software and chemometrics may be utilized for operating room conditions and may even be utilized to visualize all or a portion of a patient at one time. The colors and frequencies of the LEDs 102, 104, 106, and 108 may correspond to the types of analysis that need to be performed on the object 136, which may be a tissue or organic site or sample.

In one embodiment, the hyperspectral illuminator 100 is a multimodal imaging system that performs hyperspectral imaging including imaging chromophores, fluorescence (e.g. ICG), wound topography and volume, structured light and cross polarization for seeing into tissue (i.e. vein and lymph viewing). The hyperspectral illuminator 100 may also include a switch (not shown) for switching between modalities, such as imaging fluorescence (ICG) and HSI chromophores inherent to the tissue or injected (e.g. ultraviolet to thermal wavelengths). For example, the hyperspectral illuminator 100 and imaging system may be utilized for plastic and general surgery applications and analysis, such as skin flaps, mastectomy skin analysis, and necrosis examinations. The systems described in the embodiments may also be utilized to determine wound depth and volume, wound healing, treatment effectiveness, vein imaging, vascular clot visualization, lymph node visualization, flaps, and stitching tension to name a view potential uses.

The hyperspectral illuminator 100 may be utilized to perform imaging including spectral illumination visualizing predetermined tissue chemistry, fluorescence, or full spectral scans collecting a spectrum at each image pixel to generate a hyperspectral image data cube. For example, the hyperspectral illuminator 100 and imaging system may utilize pattern recognition to distinguish healthy tissue from unhealthy tissue and to distinguish organs. In one embodiment, the spectral illuminations cover the wavelengths ranging from 500-650 nm. However, the range is not limited and may be selected in response to chemistry and spectroscopy to be visualized which may cover the ultraviolet to infrared and beyond. Any spectrum may be utilized to visualize the location and quantity of target chemistry. For example, the LEDs may produce light at different wavelengths of the visible spectrum. Some of the LEDs may also produce white light that remains unfiltered. In one embodiment, the LEDs 102, 104, 106, and 108 may generate wavelengths varying from visible light to near infrared light or signals (and any combination thereof).

The collimators 110, 112, 114, and 116 assist in capturing and aligning the light emitted by each of the LEDs 102, 104, 106, and 108 in a narrow beam. The hyperspectral illuminator 100 includes dichroic filters 118, 120, 122, and 124 for each narrow band wavelength. In one embodiment the dichroic filters 118, 120, 122, and 124 may be arranged in an array corresponding to the LED array. The dichroic filters 118, 120, 122, and 124 are tilted at a different angle so that the band pass may be tuned for each of the LEDs 102, 104, 106, and 108. In one example, the dichroic filters 118, 120, 122, and 124 may have a range or band of 10 nm. Where four bands are required for a particular type of illumination, four LEDs and filters may be used. In another embodiment, the dichroic filters 118, 120, 122, and 124 may be custom filters that transmit two bands and as a result only one LED may be required for multiple bands. As a result, the number of LEDs or other light sources may be further reduced.

The angling of the dichroic filters 118, 120, 122, and 124 is further illustrated in FIGS. 2 and 3. The angles of the dichroic filters 118, 120, 122, and 124 may be static or variable based on the required application. In one embodiment, the angles of the dichroic filters 118, 120, 122, and 124 are set by default and may be adjusted or calibrated as needed utilizing setting and tuning components known in the art. In another embodiment, the dichroic filters 118, 120, 122, and 124 may be dynamically adjusted utilizing motors or other movable settings based on a feedback loop to tune the filter characteristics. For example, a small spectrometer may sample one or more light beams output in the illumination 132 or at other points in the hyperspectral illuminator 100. The dichroic filters 118, 120, 122 and 124 may then be adjusted so that the light beams are tuned to the required wavelengths.

The dichroic filters 118, 120, 122 and 124 further limit the light to a specific range of frequencies while reflecting the other frequencies and colors. In addition, each of the dichroic filters 118, 120, 122, and 124 may be tilted to a different angle so that the band pass may be tuned for each of the LEDs 102, 104, 106, and 108. For example, the dichroic filters 118, 120, 122 and 124 may be angularly adjusted to allow a filter designed for 600 nm to be tuned to 592 nm based on the angle-tuning properties of the dichroic coatings. In another embodiment, the hyperspectral illuminator may not require the dichroic filters 118, 120, 122 and 124 because the LEDs 102, 104, 106, and 108 produce wavelengths in specific bands required for illumination.

The integrator lenses 110 and 116 further make the filtered light more uniform. The focus lens 130 focuses the illumination 132 or output light on the illumination field 134 of the object 136. The focus lens 130 may also be utilized to configure or adjust the size of the illumination field 134. In one example the focus lens 130 may be a zoom lens adjusting the size of the illumination field 134. In one embodiment the illumination field 134 may be a two feet square for visualizing all or a portion of the abdomen and chest (with a 2-3 ft separation between the hyperspectral illuminator 100 and the tissue). For example, surgical applications may require at least 24" to be outside the minimum sterile area or dome without requiring the hyperspectral illuminator 100 be sterilized. In another embodiment, the illumination field 134 may be adjusted to view pressure ulcers or skin flaps from two to six inches squared.

The hyperspectral illuminator 100 may further include an imaging device or detector for analyzing and/or processing the interaction of the illumination field 134 with the object 136. The interactions may include reflection, absorption, fluorescence, and contrast. The hyperspectral illuminator 100 is particularly useful because the size and cost is reduced when compared with other light sources, such as an Agile Light Source (e.g. OL490). In addition, computation may be simplified by having uniform light distribution over the targeted material and selected area. The hyperspectral illuminator 100 may allow only specific wavelengths of light absorbed by the subject to illuminate the subject enhancing the signal-to-noise ratio. The hyperspectral illuminator is reduced in size because it does not require a DLP, gratings, or the associated optics. For example, the hyperspectral illuminator 100 may be a fraction of the size of the OL490 Agile Light Source while still being more than eight times as bright.

Figure 4:
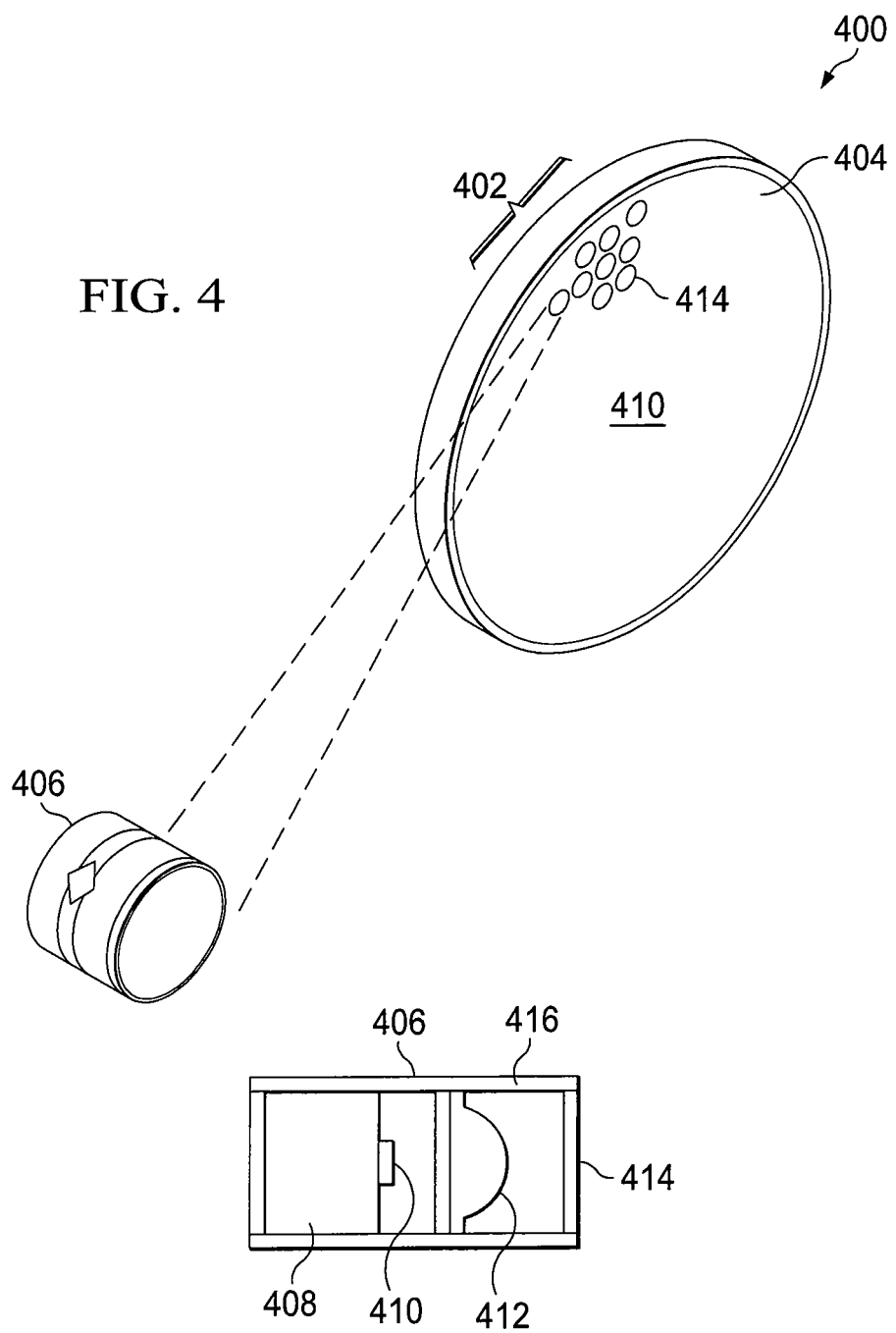
FIG. 4 is a pictorial representation of a hyperspectral illuminator 400 in accordance with an illustrative embodiment.

FIG. 4 is a pictorial representation of a hyperspectral illuminator 400 in accordance with an illustrative embodiment. The hyperspectral illuminator 400 is one embodiment that may be utilized in an operating room light for performing hyperspectral imaging when coupled with an imaging camera, managing software, and chemometrics. As shown, the hyperspectral illuminator 400 may include an LED array 402. The LED array 402 may be embedded or integrated in a frame 404. In one embodiment, individual LEDs of the hyperspectral illuminator may be removed, replaced, or reconfigured for different applications.

In one embodiment, each of the LEDs of the LED array 402 may be color coordinated or otherwise marked indicating a specified wavelength. As a result, the LED array 402 may be more easily configured for specified types of testing.

Each of the LEDs within the LED array 402 may be composed of individual units, such as LED unit 406. The LED unit 406 may include a heat sink 408, LED 410, collimator 412, and dichroic filter 414. The components of the LED unit 406 may be enclosed in a case 416. In one embodiment, the hyper spectral illuminator 400 is an integrated portion of an overhead light, such as a surgical light.

Figure 5:
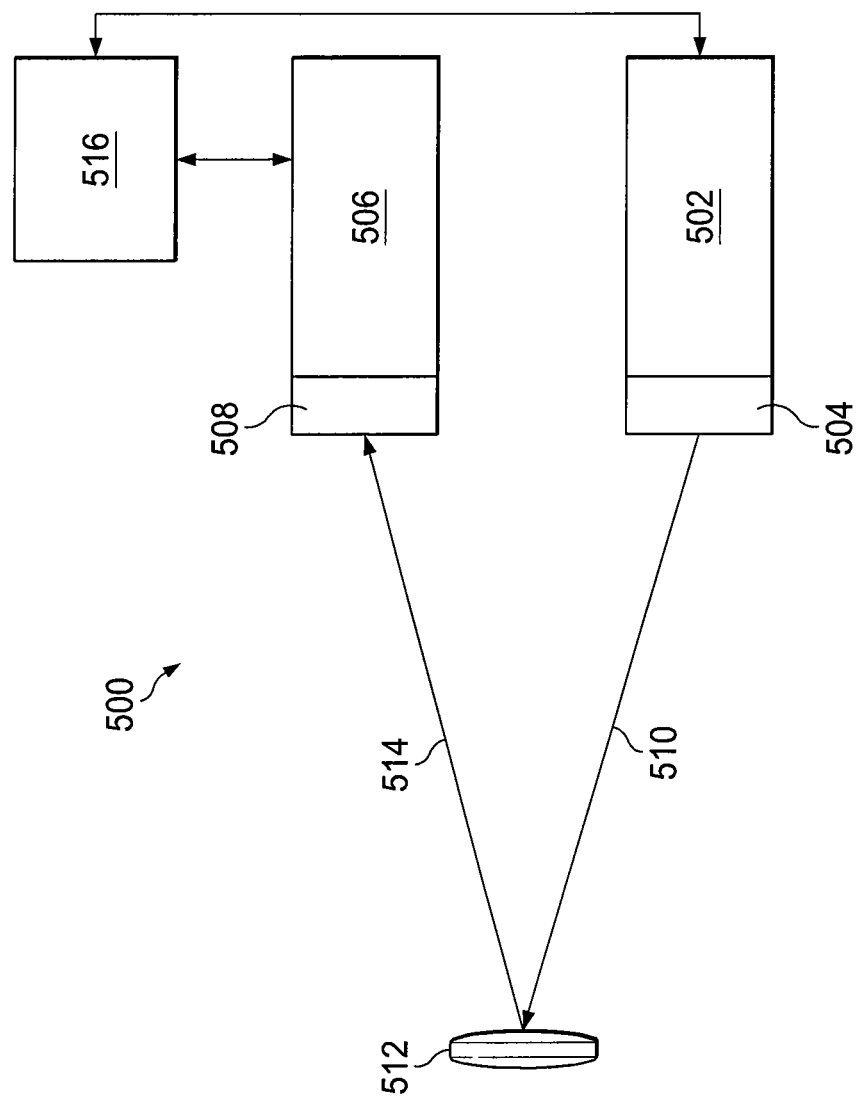
FIG. 5 is a block diagram of an imaging system 500 in accordance with an illustrative embodiment.

FIG. 5 is a block diagram of an imaging system 500 in accordance with an illustrative embodiment. The imaging system 500 may include a hyperspectral illuminator 502 including a source circular polarizer 504 and a detector 506 that may include a detector circular polarizer 508. The hyperspectral illuminator 502 or source may output linearly polarized light 510 that is reflected off of tissue 512 as un-polarized light 514.

The source circular polarizer 504 linearly polarizes the output light (parallel or 0° with respect to the hyperspectral illuminator 502) passed to the tissue 512 as linearly polarized light 508. In one embodiment, the detector circular polarizer 508 may have a plane of polarization of approximately 45-50° relative to the source circular polarizer 504 to reduce glare. The light that passes through the detector circular polarizer 508 is then passed to the detector 506 for processing and additional analysis. The source circular polarizer 504 and detector circular polarizer 508 may include threads for attachment to the hyperspectral illuminator 502 and the detector 506. Cross polarization provides an improved image and the ability to see further into the tissue. The detector 506 may be any number of systems including a focal plane array, such as CCD, and CMOS that is typically utilized in video cameras, cameras, web cams, or imaging devices known in the art. The detector 506 may also include any number of custom or off the counter lenses, such as 50 or 60 mm Nikon lenses.

In one embodiment, the imaging system 500 may determine tissue oxygenation. In addition, thresholds for the tissue or target may be associated with automatic alerts, such as audio alerts, graphical displays of information, outlining the tissue that is above or below the threshold, or otherwise alerting and displaying information to a user. For example, a threshold of approximately 60-62% HbO2 may provide information regarding incision points, viable tissue, delayed healing, or potential necrosis. A tissue threshold of 60+/−2% $HbO_2$ being blow this threshold increases the risk for post operative necrosis in skin flap surgery. In another example, during kidney surgery the 70-80% $HbO_2$ range may be associated with a kidney that may withstand long surgery times and still have normal post operative kidney function. Kidneys below 70% $HbO_2$ may result in below normal post operative kidney function when ischemic for long periods of time.

For example for skin flaps a threshold below 62% has been associated with post operative necrosis and increased recovery times and hence a risk factor predicting the possibility of post operative necrosis. The imaging system 500 may utilize any number of thresholds or alerts to indicate to a user that the threshold is exceeded. A surgeon may utilize real-time images to plot gradients, make marks, or make incisions. In one embodiment, the imaging system 500 may utilize a variable exposure time. For example, with a 3-shot method a ratio of 3.87:1.95:1, but not limited to such a ratio may be utilized. The combination of illumination intensity provided by source along with exposure time of the detector as the detector varies from one illumination to the other. The imaging system 500 may also compensate or correct for optical effects or medical conditions, such as melanin or curvature. For example, compensation may be performed by varying the chemometric threshold that compensates for melanin levels and structured lighting for curvature.

The imaging system 500 may further include processing unit 516 (a data processing system) utilized to process the images, video, or data acquired by the detector 506. In one embodiment, the processing unit 516 may be a laptop, desktop computer, PDA, smart phone or other device that processes the data for display to a user or a custom circuit board or be a field programmable gate array. The processing unit 516 may be further utilized to control the hyperspectral illuminator 502 for illuminating the tissue 512. The processing unit 516 may utilize any number of graphical user interfaces to receive control commands, instructions, and information. The processing unit 516 may also be utilized to compensate for reflectance issues and problems from the complex spectral light reflected off of the tissue 512 the processing unit 516 may process and display chemically encoded images at or near video rates. The processing unit 516 may utilize software or firmware for performing the processing and displaying. The processing unit 516 may also utilize chemometric algorithms to ensure that the tissue 512 is properly illuminated and the reflected light is properly analyzed for displaying tissue chemistry quantitatively. In other embodiments, the processing unit 516 may be an application specific integrated circuit, field programmable gate array, or other enhanced processing unit.

Turning now to FIGS. 6-12, FIG. 6 is a pictorial representation of a hyperspectral illuminator 600 in accordance with another illustrative embodiment. The hyperspectral illuminator 600 may be similar to the embodiment shown in FIGS. 1-3. The hyperspectral illuminator 600 may be configured and packaged for utilization in any number of surgical, clinical, research, or other settings. One embodiment, the hyperspectral illuminator 600 may include a number of LEDs and filters to produce at least a first and illumination spectrum, a second illumination spectrum and a third illumination spectrum.

Figure 7:
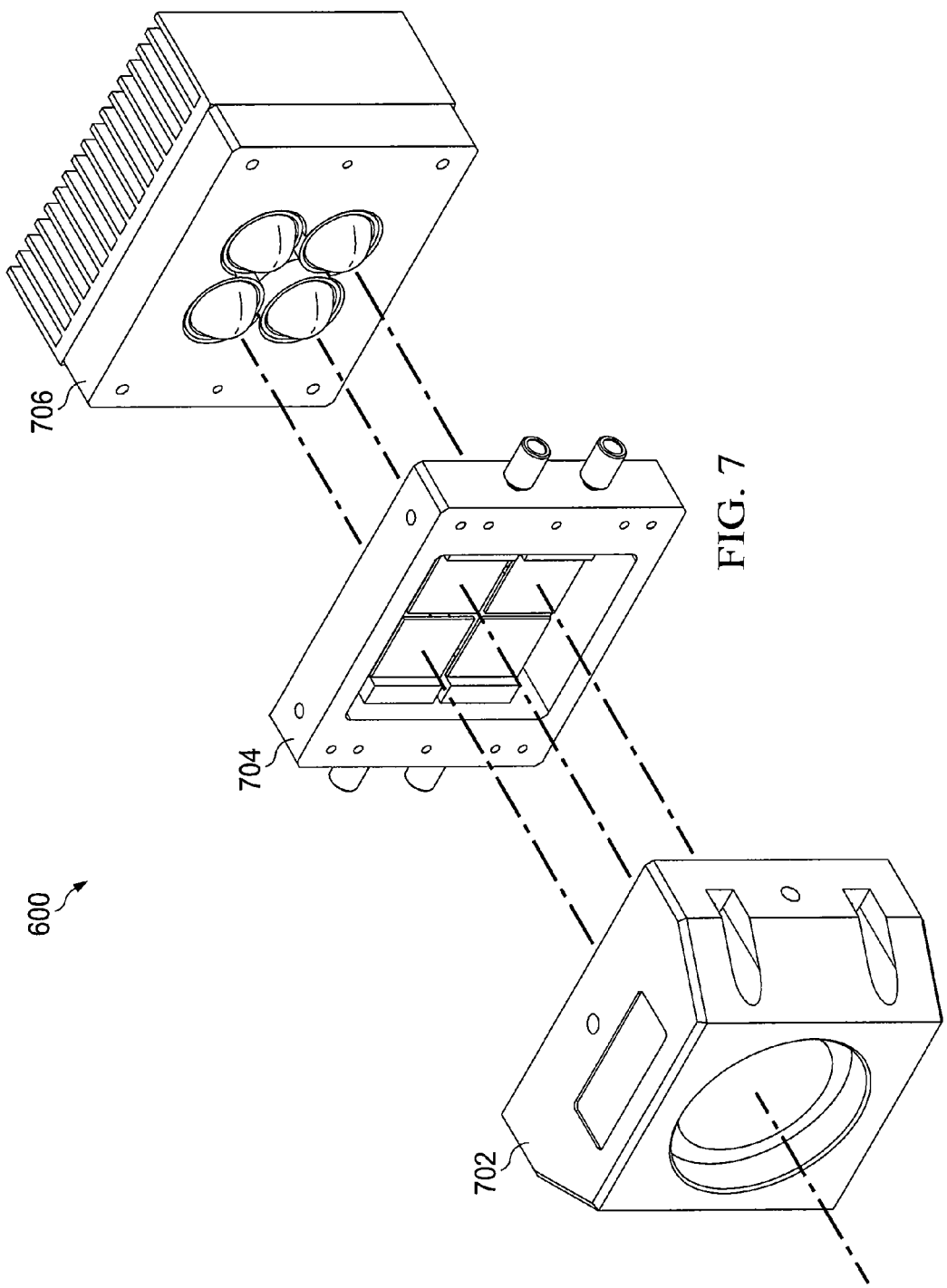
FIG. 7 is an exploded view of the hyperspectral illuminator 600 of FIG. 6.

The hyperspectral illuminator 600 may be composed of a number of components or modules as is shown in the exploded view of FIG. 7. In one embodiment, the hyperspectral illuminator 600 may include a projection optics module 702, a dichroic module 704, and an illumination module 706. The modules of the hyperspectral illuminator 600 may be connected, integrated, or attached utilizing any number of attachment devices or securing mechanisms. For example, buckles, pins, set screws or other connectors may be utilized to both align and secure the modules of the hyperspectral illuminator 600 to one another.

In one embodiment, the hyperspectral illuminator 600 may be enclosed in a portable and small framework, similar to a mini to large flashlight. The hyperspectral illuminator 600 may also be configured to include the detector/camera and other processing components for a mobile embodiment. The hyperspectral illuminator 600 may also be embodied in an endoscope. The hyperspectral illuminator 600 may include a battery (not shown) or other power connection for powering a portable embodiment.

In another embodiment, the hyperspectral illuminator 600 may be entirely encompassed within an application specific integrated circuit (ASIC), fully programmable gate array (FPGA) with illumination functionality (e.g. programmable LEDs), or other similar circuit.

Figure 6:
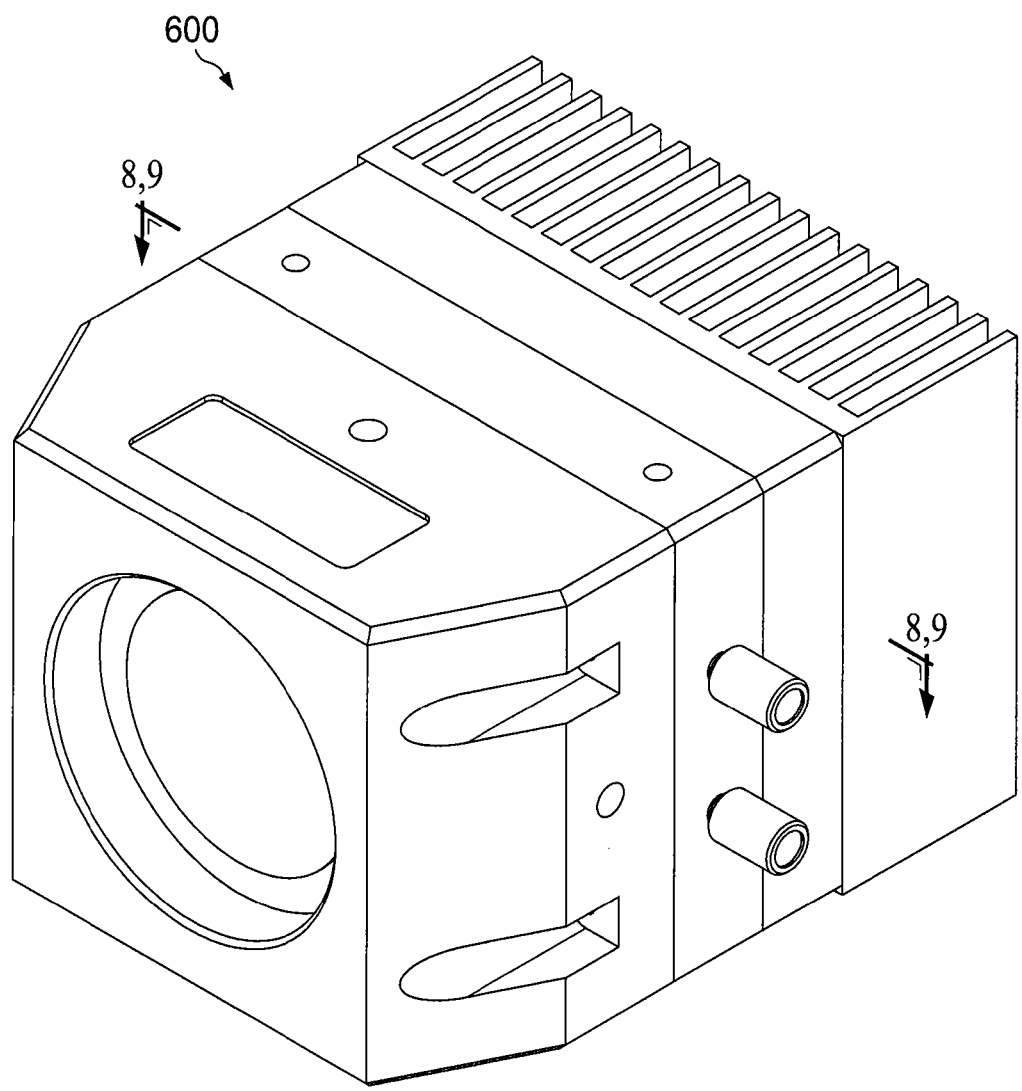
FIG. 6 is a pictorial representation of a hyperspectral illuminator 600 in accordance with another illustrative embodiment.
Figure 8:
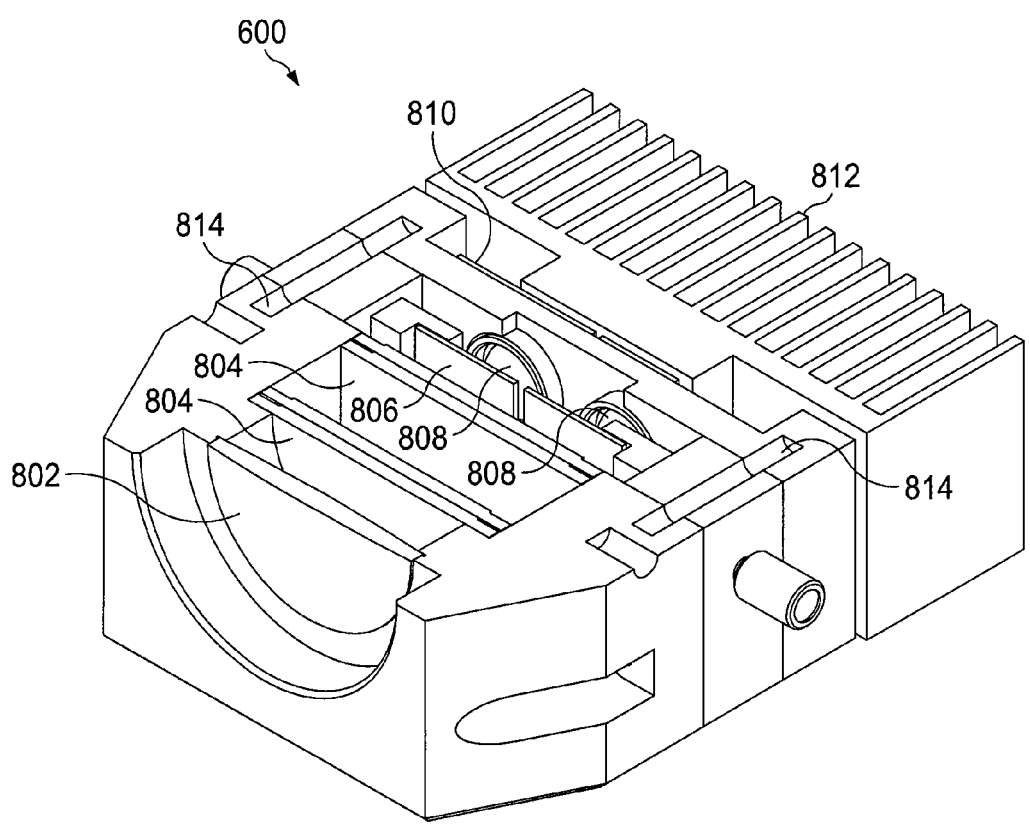
FIG. 8-9 are cut-away views of the hyperspectral illuminator 600 of FIG. 6.
Figure 9:
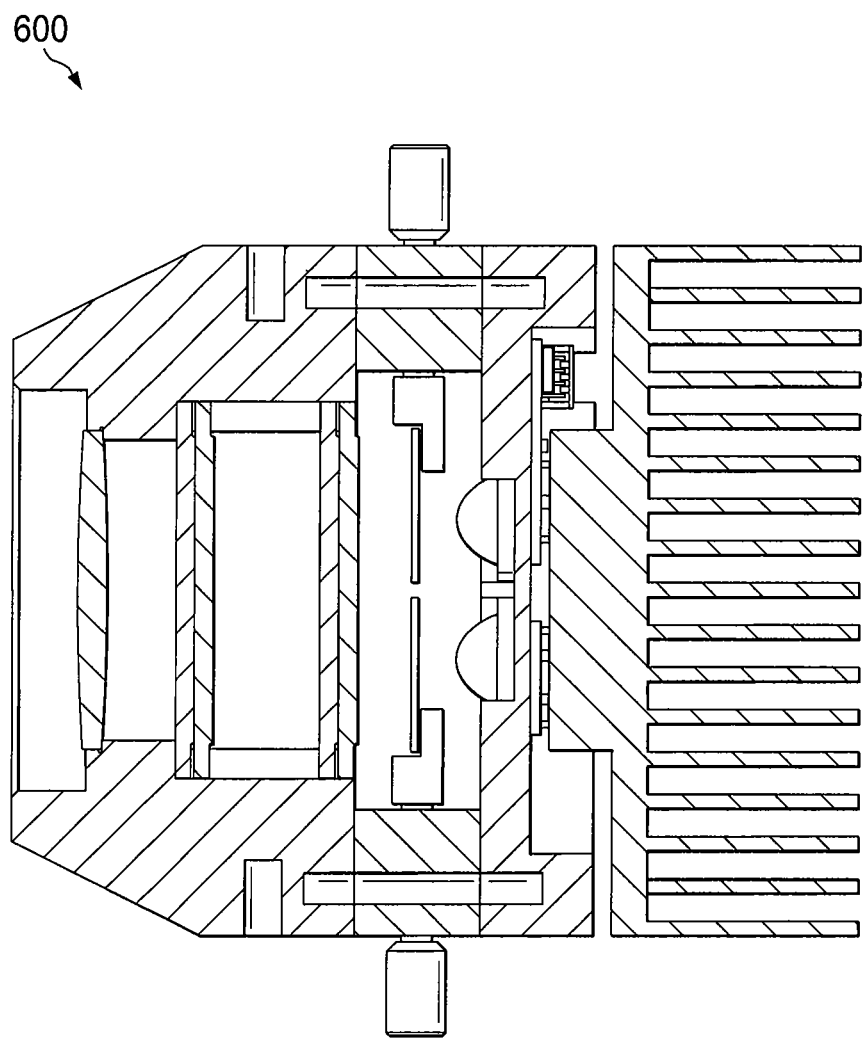

FIGS. 8-9 are a cut-away view of the hyperspectral illuminator 600 of FIG. 6. The hyperspectral illuminator 600 may include a first lens 802, fly eye lenses 804, dichroic filters 806, collimator lenses 808, LED printed circuit boards (PCB) 810, a heat sink 812, and alignment holes 814. In addition, the hyperspectral illuminator 600 may include any number of retainer rings, spacers, and other securing and separating components not specifically called out. For example a retainer ring may keep the first lens 802 in position and a fly eye spacer (not shown) may separate the fly eye lenses 804. The hyperspectral illuminator 600 may also include threading for screwing in a circular polarizer as previously described.

Figure 10:
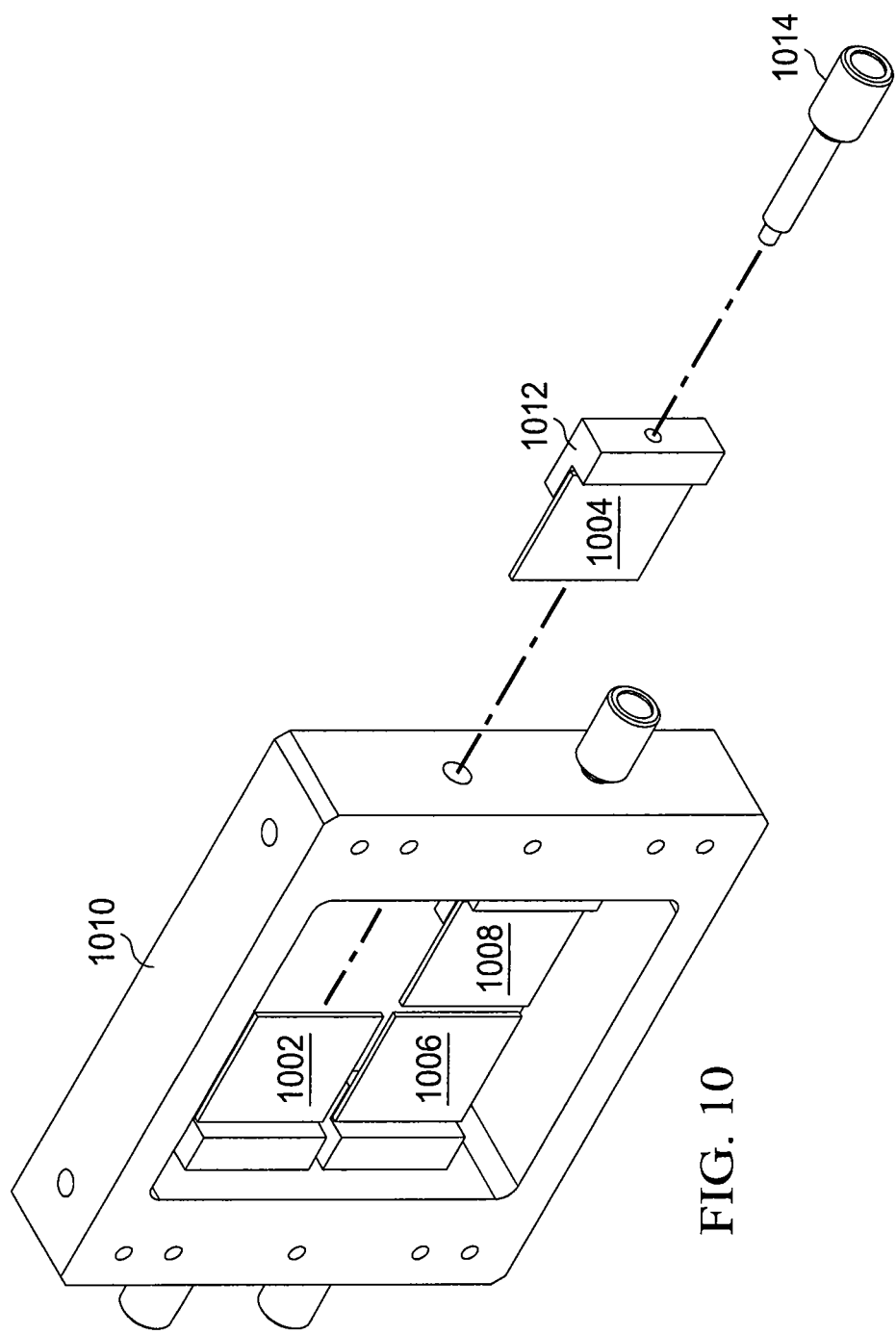
FIG. 10 is a pictorial representation of a dichroic module in accordance with an illustrative embodiment.

FIG. 10 is a pictorial representation of a dichroic module 1000 of the hyperspectral illuminator of FIG. 6. The dichroic module 1000 may include a number of dichroic filters. In one embodiment, the dichroic module 1000 includes four dichroic filters 1002, 1004, 1006, and 1008. As illustrated a system chassis 1010 may house the dichroic filters 1002, 1004, 1006, and 1008. In one embodiment uniformly applicable, the dichroic lens 1004 may be secured by a mount 1012. The position of the dichroic filter 1004 and mount 1012 may be adjusted by a connected pivot knob 1014. One or more set screws 1016 may fix the position, tilt and angle of the dichroic filter 1004 and mount 1012 when positioned in the system chassis 1010. The system chassis 1010 includes a number of holes for fixing each of the dichroic filters 1002, 1004, 1006, and 1008.

Figure 11:
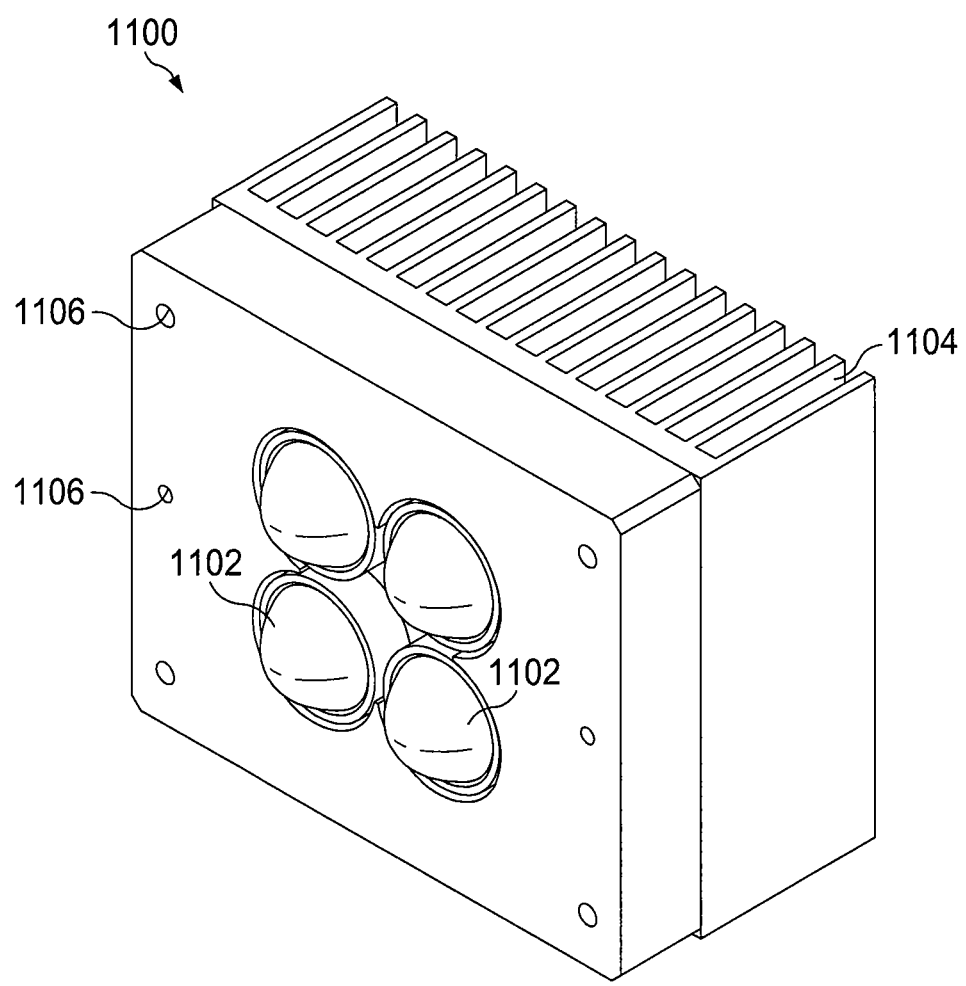
FIG. 11 is a pictorial representation of an illumination module in accordance with illustrative embodiment.

FIG. 11 is a pictorial representation of an illumination module 1100 in accordance with illustrative embodiment. The illumination module 1100 may include an LED array 1102, a heat sink 1104, and mounting holes 1106. As previously described, the LED array 1102 may include any number of LEDs positioned in any number of configurations. The heat sink 1104 may be utilized to cool the hyperspectral imager during usage and may include any number of passive or active cooling systems, such as fans, fans, liquid cooling, and so forth.

The mounting holes 1106 may be utilized to attached the components of the illumination module 1100 or two attached the illumination module to the other modules of the hyperspectral illuminator.

Figure 12:
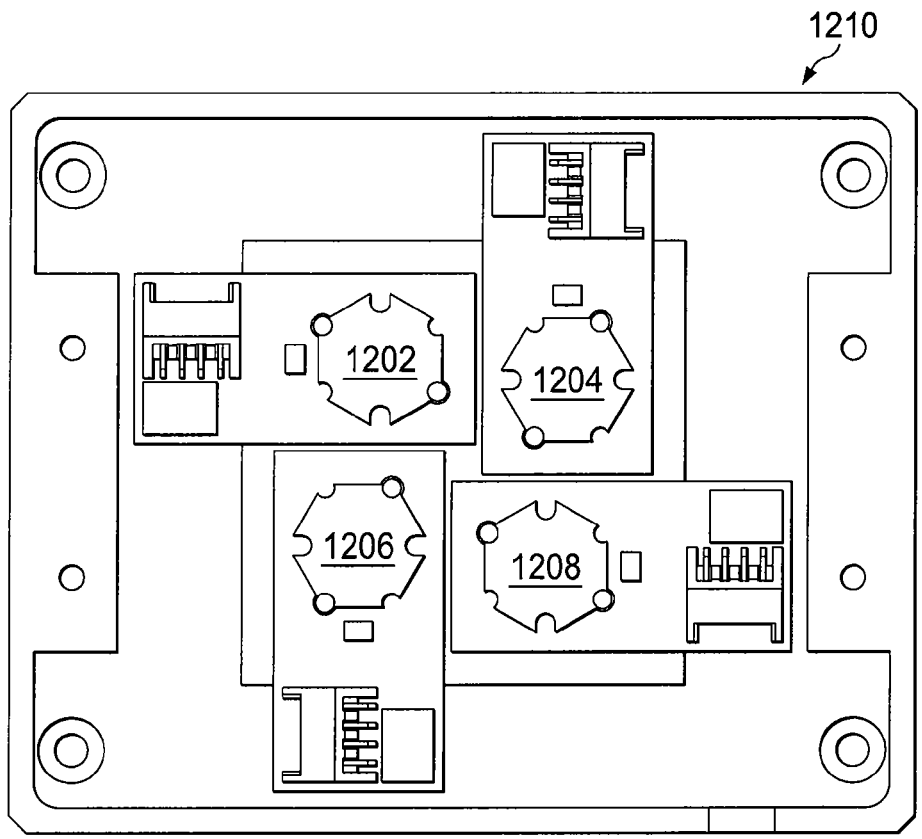
FIG. 12 is a pictorial representation of the LED printed circuit boards in accordance with an illustrative embodiment.

FIG. 12 is a pictorial representation of the LED printed circuit boards 1202, 1204, 1206, and 1208 in accordance with an illustrative embodiment. As the included embodiment, each of the printed circuit boards 1202, 1204, 1206, and 1208 is a separate component. As a result, the printed circuit boards may be more easily replaced for maintenance or repair or reconfigured to provide specified wavelengths.

The LED printed circuit boards 1202, 1204, 1206, and 1208 may be connected to a chassis 1210. The collimators (not shown) may be attached to the other side of the chassis 1210 corresponding to each of the LEDs mounted in the LED printed circuit boards 1202, 1204, 1206, and 1208. In another embodiment, the printed circuit boards 1202, 1204, 1206, and 1208 or the respective heat sinks may be integrated in a single printed circuit board. A single printed circuit board may share power and control components, such as buses, ports, interfaces, or so forth. In another embodiment, the printed circuit board may also include a processor and a memory for storing instructions utilized to control the hyperspectral illuminator.

Figure 13:
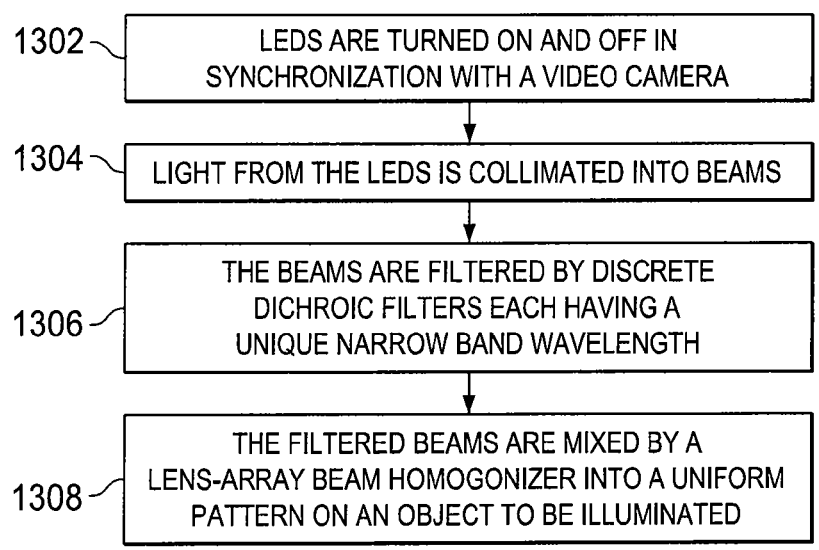
FIG. 13 is a flowchart of a process for hyperspectral illumination in accordance with an illustrative embodiment.

FIG. 13 is a flowchart of a process for hyperspectral illumination in accordance with an illustrative embodiment. The process of FIG. 13 may be implemented by a hyperspectral illuminator. The process may begin with multiple LEDs being turned on and off in synchronization with a video camera (step 1302). The number and color of the LEDs may be selected in response to the target material being analyzed and imaged. Any number of switching components may be utilized to control the operation of the LEDs. In one embodiment, a control module triggers the LEDs and control the camera imaging and data collection as required. The control module may also control the processing of the data utilizing pipeline processing. For example the LEDs are triggered to illuminate using ill1 and then the camera is triggered to capture the reflectance image of ill1 followed by ill2 and ill3, which are then digitized and all three are processed accordingly. In another embodiment, only one new illumination is collected and digitized, and then processed using the previous two illuminations for determining the chemically encoded image. Another embodiment may include synchronizing the hardware trigger and using a parallel processing thread to process the collected digitized images in parallel for triggering the hardware in synchrony and digitization.

Next, light from the LEDs is collimated into beams (step 1304). The beams are filtered by discrete dichroic filters each having a unique narrow band wavelength (step 406). The frequency of the light is determined by the selection of dichroic filters.

Next, the filtered beams are mixed by a lens-array beam homogenizer into a uniform pattern on an object to be illuminated (step 1308). In one embodiment, the lens-array beam homogenizer is one or more integrator lenses. The lens-array may also be a fly eye lenses for projecting the filtered beams uniformly (e.g. intensity and color). The beams may also be passed through a focus lens to focus the beams to define the illumination field. The output light of the illumination spot or field may configured to emit any number of shapes including round, hexagonal, square, rectangular, and so forth. A zoom system may be utilized to vary the size of the illumination spot.

Figure 14:
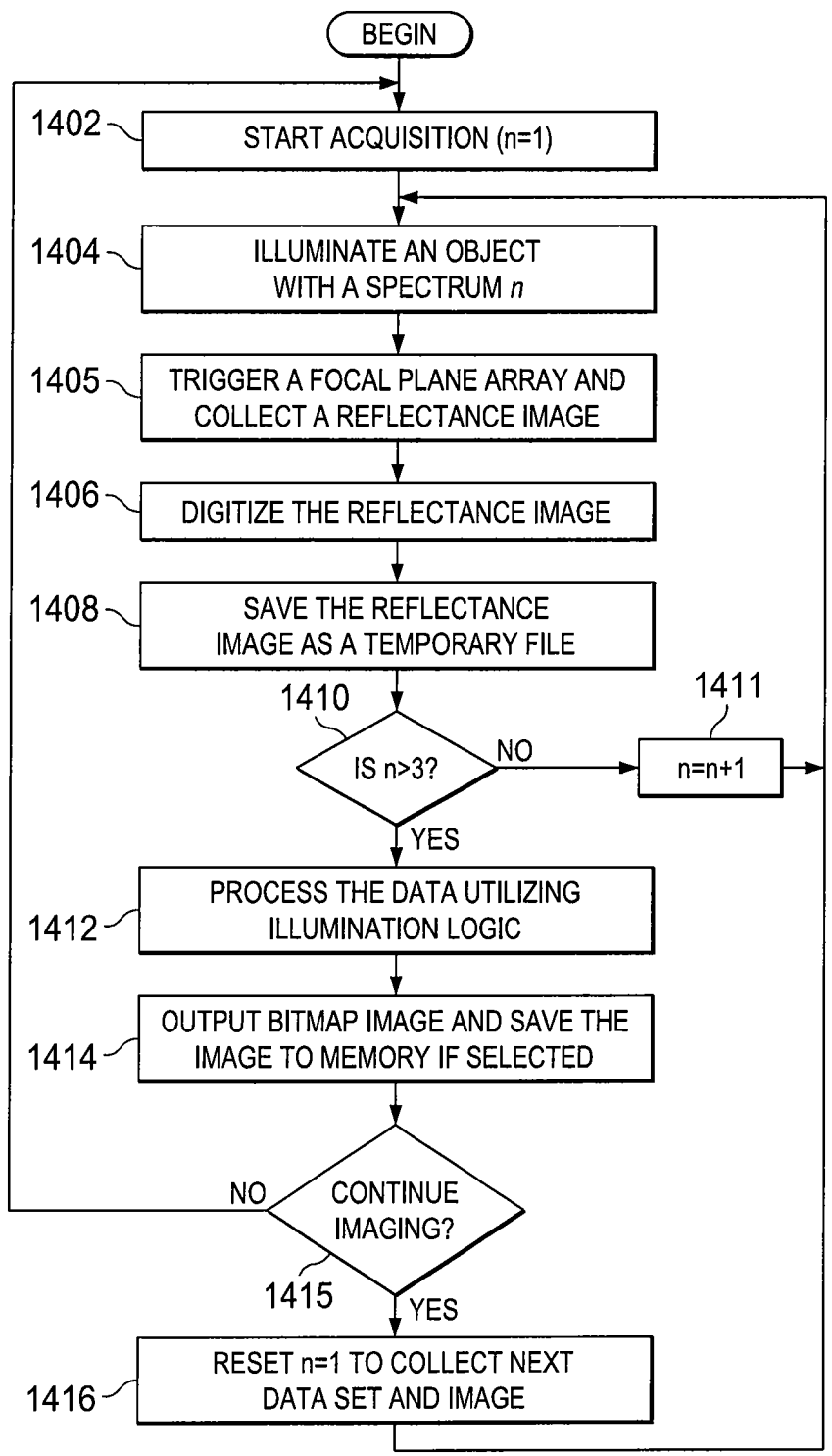
FIG. 14 is a flowchart of a process for multiple illuminations in accordance with an illustrative embodiment.

FIG. 14 is a flowchart of a process for multiple illuminations in accordance with an illustrative embodiment. The process of FIG. 14 may be implemented by a hyperspectral imaging system as described in the illustrative embodiments. In one embodiment, the system may be configured to utilize pre-set parameters, characteristics, settings, or conditions. In another embodiment, the system may utilize experimental parameters. As a result, the system and processes utilized may constantly change for different patients and requirements. The process may begin with the system starting acquisition with n=1 (step 1402). In one embodiment, the user may select to begin acquisition utilizing a graphical user interface displayed by the system. For example, the user may be a doctor that is examining a skin flap of a patient and has turned on or otherwise activated the system. In another embodiment, acquisition may begin automatically in response to detecting that an object, such as tissue or an appendage has been positioned within the field of view.

Next, the system eliminates an object with a spectrum n (step 1404). In one embodiment, the system may activate a hyperspectral illuminator or LED head to illuminate the object. The spectrum may be selected automatically utilizing a defined process. In another embodiment, the user may set the spectrum for each illumination (i.e. n=illumination 1, illumination 2, illumination 3).

Next, the system triggers a focal plane array and collects a reflectance image (step 1405). During step 1405 the focal plane array (FPA) may be triggered to collect a spectroscopic reflectance image (image/data capture). Step 1405-1408 may all be performed by a camera of an imaging system to open the shutter of the camera, detector, or array, expose the FPA, close the shutter, and perform analog-to-digital conversion. The system may utilize a variable exposure time to maximize the signal to noise ratio. For example, the ratio may be 3.87:1.95:1 relative to a three illumination cycle for ill1, ill2, and ill3 (or illall). However, any number of ratios may be utilized to reduce noise and enhance image quality.

Next, the system digitizes the reflectance image (step 1406). As noted, step 1406 may include analog-to-digital conversion by any number of devices or components of the image array.

Next, the system saves the reflectance image as a temporary file (step 1408). The data saved in the temporary file may be saved in the raw spectroscopic reflectance image array as well as the digitized or processed format for additional processing and analysis. For example, the data may be saved as temp00n.dat. The data may be temporarily saved to a RAM memory, and if selected, may also be streamed to a long-term memory (e.g. hard drive). During steps 1404-1408, the system may perform hardware synchronization to synchronize illumination, triggering, and data/sensor capture of the illumination and detection modules of the system.

Next, the system determines whether n is greater than 3 (step 1410). The illustrative embodiment is shown utilizing a three shot process. However, the system may utilize any number of illumination combinations to acquire the data and images necessary for the user. If n is not greater than 3, the system sets n equal to n+1 (step 1411) before returning to illuminate the object at the spectrum n (step 1404). By repeating step 1404, data may be acquired at different wavelengths and spectral illumination combinations in order to generate a composite image. The different spectral combinations may be set by a predetermined algorithm specified for the tissue or wound type, patient needs, If n is determined to be greater than 3 in step 1410, the system processes the data utilizing illumination logic (step 1412). For example, the illumination logic may be an algorithm implemented as a script, program, or application. The system outputs a bitmap image and saves the image to memory selected (step 1414). During step 1414 the raw reflectance spectroscopic image array may also be saved to memory. Any number of image or output files or formats may be utilized. The image (final chemically encoded processed image and raw reflectance images ill1, ill2, and ill3) may also be saved to a temporary or long term memory or database in response to a user selection. The user selection may be received through the graphical user interface prior to starting or during the acquisition process of FIG. 14. During step 1414 the image may be displayed to one or more users in real-time or near real-time for utilization as is herein described. The data set acquired may be utilized to generate a hyperspectral image utilizing the different spectrums. The data sets may also be utilized to generate a hyperspectral image cube.

Next, the system determines whether to continue imaging (step 1415). The determination may be made based on user feedback or in response to an automatic decision. For example, the system may determine that a tissue sample has been thoroughly illuminated and imaged with all of the required or specified illumination spectra. If the system determines to stop imaging during step 1415, the process ends.

If the system determines to continue image during step 1416, the system resets n equal to one to collect the next data set an image (step 1416). After step 1416, the system may again return to step 1404 to start acquisition for determining the next chemically encoded image in time or use different processing methods. For example, only collecting ill1 and using the current ill1 with the previous ill2 and ill3 to determine the current chemically encoded image or utilizing a different set of spectra or wavelengths. For example, the spectrum associated with n may vary between data sets. In addition, the system may perform post image processing of stored images and then store/display the chemically encoded visualization for real-time usage.

The process illustrated in FIG. 14 is not limited to collecting only three spectral images and performing processing. For example, a new n1 image may be acquired and the old or previous n2 and n2 images from the previous data set may be utilized to calculate and determine the chemically encoded image. The process of FIG. 14 may be utilized as management logic (hardware or software) for the real-time flow of data including: synchronizing hardware, collecting data, processing the data, and visualizing and storing the data.

Figure 15:
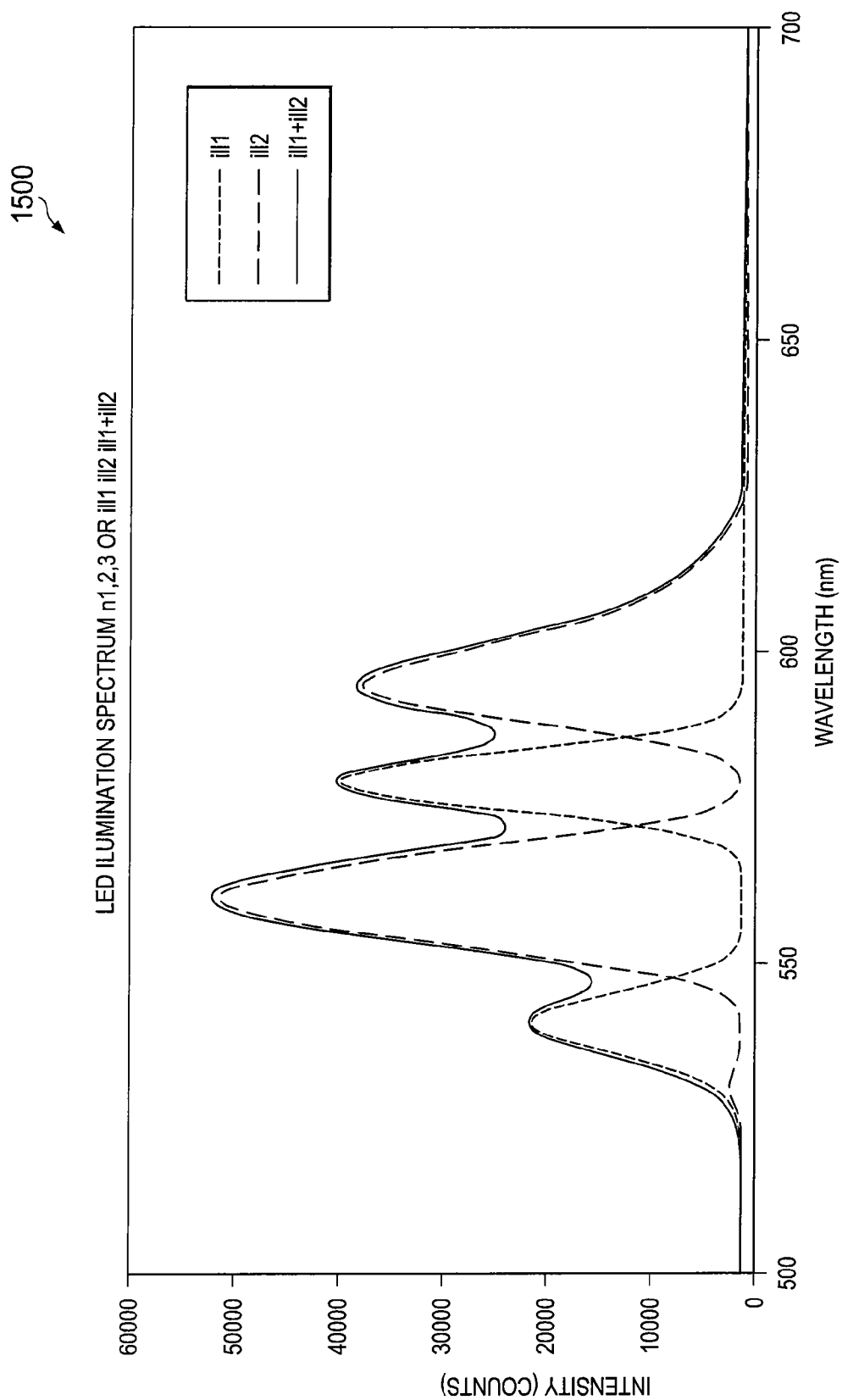
FIG. 15 is a representation of illumination spectra in accordance with an illustrative embodiment.

FIG. 15 is a representation of illumination spectrums 1500 in accordance with an illustrative embodiment. The illumination spectrums shown in FIG. 15 may correspond to those utilized in the process of FIG. 14. For example, n=1 may correspond to ill1, n=2 may correspond to ill2, and n=3 may correspond to ill3 (or ill1+ill2). In one embodiment, the first spectral illumination (ill1) is the positive spectral difference determined by subtracting the normalized parent absorbance spectrum of Hb from HbO2. The second illumination (ill2) subtracts HbO2 from Hb, and the third illumination (ill3) is a broadband spectrum of the source or all LEDs. The three complex spectroscopic illuminations reflected from the tissue or object are measured at each detector image pixel and processed by determining a difference image between the ratios of the first two reflected illuminations to the bright field image. The resulting chemical encoded images allow the user, such as a surgeon, to monitor changes in blood oxygenation perfusion. FIG. 15 illustrates spectra that may be utilized in one embodiment.

As previously noted hyperspectral imaging is the process of collecting and utilizing multiple spectra composed of multiple wavelengths for determining the chemical nature of an object, sample, or material. Hyperspectral imaging systems are may be utilized in a number of venues to provide highly-relevant real-time mapping and visualization data, chemically encoded images, and other images and information to assist surgeons, researchers, physicians, and other professionals. The ill1+ill2 (illall) provides a background that may be utilized to compare against different waveforms to view the chemical analysis.

Figure 16:
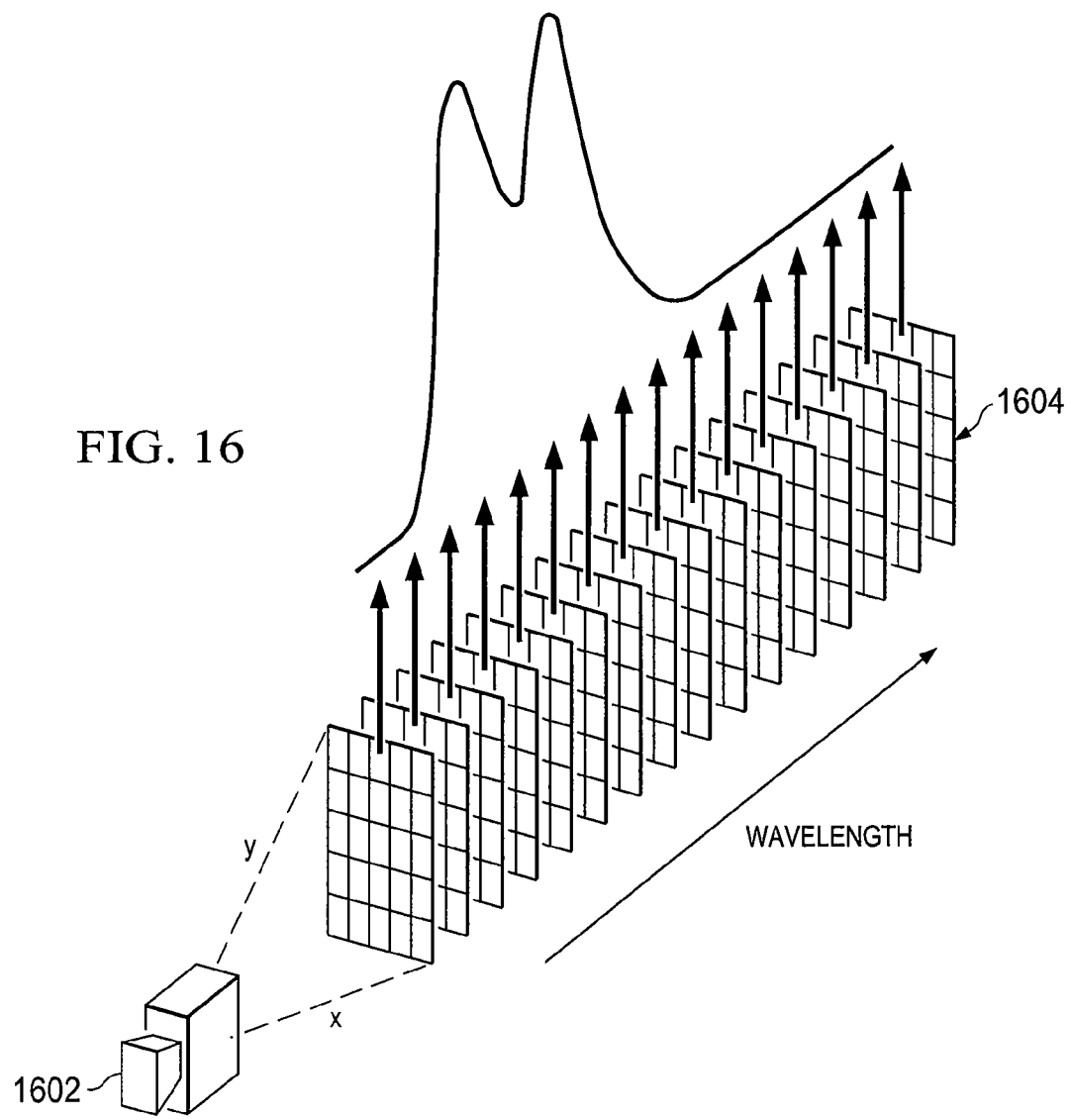
FIG. 16 is a representation of imaging data being utilized to generate a hyperspectral image cube in accordance with an illustrative embodiment.

FIG. 16 is a representation of imaging data being utilized to generate a hyperspectral image cube in accordance with an illustrative embodiment. As is previously described, the illustrative embodiments may augment visualization of chemical components of interest by selecting spectra are utilized to illuminate tissue or a site for analysis. The spectra may include visible light as well as UV, IR, and NIR. For example, UV may be utilized to visualize carcinomas. In one embodiment, an imaging system 1602 including a synchronized source and detector generates a series of images 1604. The images 1604 may be captured utilizing multiple wavelengths with narrow or broad spectral bandwidths or continuous complex spectral illumination. Each of the images 1604 may correspond to specific spatial location or spectral information. For example, as shown, the images 1604 may represent a series of wavelength dependent image planes. The hyperspectral image data of FIG. 16 may be compiled as a 3-dimensional data cube consisting of two dimensions (x, y) imaging the field of view as a function of wavelength (z) the third dimension.

Various multivariate analysis methods, end member, or classification methods may be utilized. The spectroscopic data collected by the imaging system and formatted into a 3-dimentional hyperspectral image cube as shown in FIG. 16, may be utilized for quantifying the chemistry of interest. Analyzed chemistry may include HbO2, Hb, MetHb, HbNO, H20, myoglobin, autofluorescence of Leukocytes, collagen, neutrophols, tryptophan NADPH, bacterial and fungal infections and possibly using one spectral illumination for visualizing several of the above chromophores and fluorophores simultaneously. The acquisition of images at multiple wavelengths with narrow or broad spectral bandwidths may be utilized for complex spectral illumination. For example, an array of wavelength dependent image planes may be imaged and utilized. For example collagen may be excited in the UV 270-370 nm range for applications regarding osteoarthritis. Melanin may be excited from 340-400 nm, such as to perform melanoma detection. In addition, NIR wavelengths (approximately 820-880 nm) may be utilized for imaging the vasculature. A multi-modal imaging approach may be utilized to visualize the % HbO2 within the microvasculature (capillaries) within ~0.75 mm of the skin (visible light) versus an image using NIR light visualizing the % HbO2 from the larger deeper blood vessels and mapping the large blood vessels.

Figure 17:
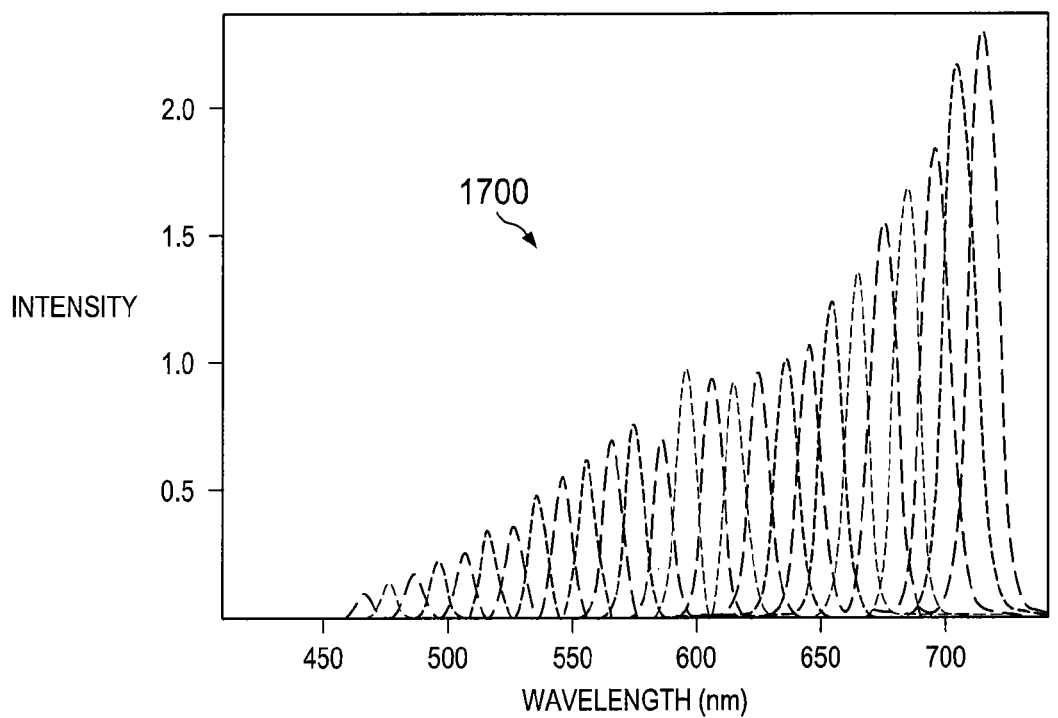
FIG. 17 shows a graph illustrating sequential wavelength illumination in accordance with an illustrative embodiment.
Figure 18:
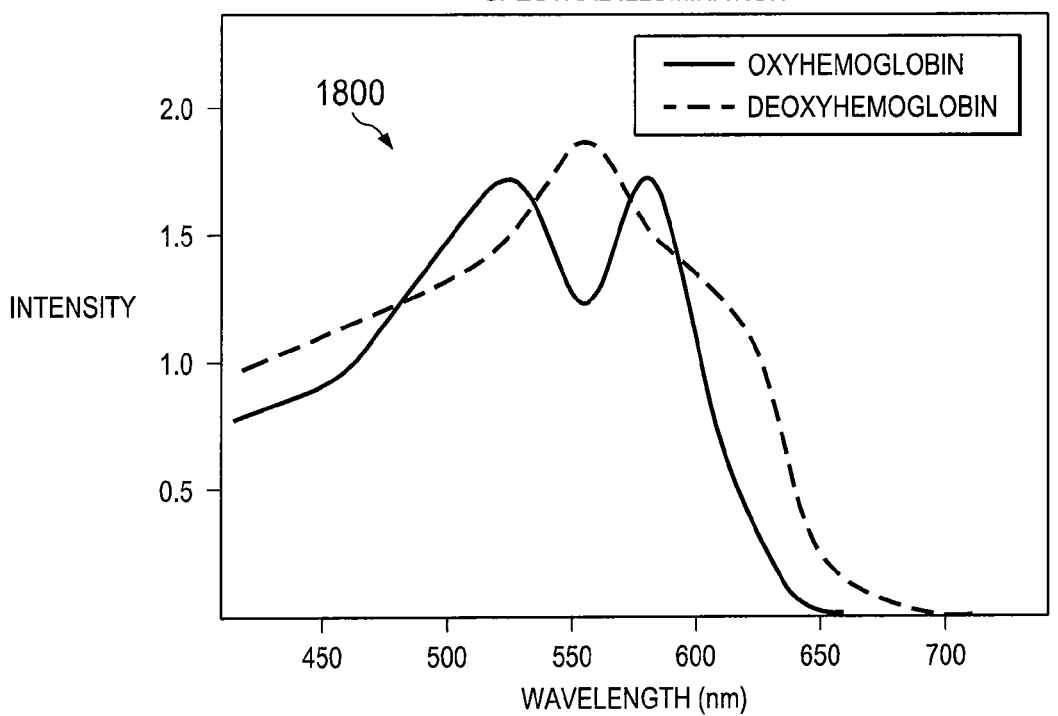
FIG. 18 shows a graph illustrating complex spectral wavelength illumination in accordance with an illustrative embodiment.

FIG. 16 further illustrates how data and images are formatted after being collected or acquisitioned. Chemometrics are utilized to apply supervised or unsupervised multivariate mathematics to hyperspectral image data collected over a field of view for visualizing and extracting chemical characteristics and nature of an object, such as tissue. Traditional spectroscopy has focused on illuminating a sample/tissue with white or broadband light, and then collecting spectra (transmitted or reflected) which is then processed using math for identifying chemistry of the sample/tissue. FIGS. 17 and 18 show examples of active hyperspectral illumination schemes that may be utilized to generate the hyperspectral image cube. Acquired images may be overlaid, stacked, or displayed side-by-side. In one embodiment, the system may automatically display an alert in response to determining blood flow is below a threshold. The portions of the target that are below the threshold may be marked in a different color, highlighted using the illumination system or a secondary illumination system, or marked with text on a display indicating the levels in text and/or numbers utilizing the imaging system or a display receiving content from the imaging system.

FIG. 17 shows a graph 1700 illustrating sequential wavelength illumination in accordance with an illustrative embodiment. The graph 1700 illustrates the wavelength (x-axis) and the intensity (y-axis) utilized for illumination for one embodiment where sequential illumination is performed with a series of 126 band passes.

FIG. 18 shows a graph 1800 illustrating complex spectral wavelength illumination in accordance with an illustrative embodiment. The graph of 1800 similarly illustrates two complex spectra and the oxyhemoglobin and deoxyhemoglobin characteristics that may be determined utilizing the associated wavelengths. The illustrative embodiments utilize active illumination to illuminate the sample/tissue with one or more selected spectra to determine how much of a known chemical is present.

The described embodiments for hyperspectral imaging provide a clinical imaging platform that may analyze the presence and amounts of various chromophors and fluorophores within objects or organic materials, such as skin. Hyperspectral imaging aids doctors, clinicians, and scientists in predicting, detecting, monitoring, and assessing skin, skin flaps, skin grafts, skin diseases (e.g. pressure ulcers), and wounds. Hyperspectral imaging may visualize the chemical nature of skin. The imaging and visualization may be performed or controlled in vivo, non-invasively, remotely, and at, near, and beyond video rates using the principles of chemical physics, spectroscopy of chromophors, or inherent autofluoresce of the tissue. The imaging and visualization may also be exogenously introduced (infused or injected) chromophors and fluorophores.

The illustrative embodiments are applicable to wounds in general, which may include, but are not limited to sores, ulcers, pressure ulcers, peripheral ulcers, bed sores, diabetic and lower limb diabetic ulcers, venous ulcers, lesions, burns, skin flaps, peripheral vascular disorders, or stitches. The illustrative embodiments may also be utilized alone or as integrated with an endoscope, surgical microscope, fundus camera, and slitlamp, or in other system configurations to perform intra-operative bile duct visualization, improve postoperative outcomes, monitor partial nephrectomy, monitor renal ischemia, retinal imaging, diabetic retinopathy, macular degeneration, jaundice, non-invasive optical biopsies, pharmaceutical development, micro-vascular surgery, and neurosurgery to name a few. The illustrative embodiments may be utilized for plastic surgery, GI endocrine surgery, neurological surgery, urology, ophthalmology, clinical monitoring, digital pathology, and pharmaceutical development. Some non-medical applications may include food safety monitoring (i.e. pathogens such as salmonella), monitoring aircraft and power plants for debris (i.e. metal shavings), determining viscosity of petroleum products, and so forth.

Figure 19:
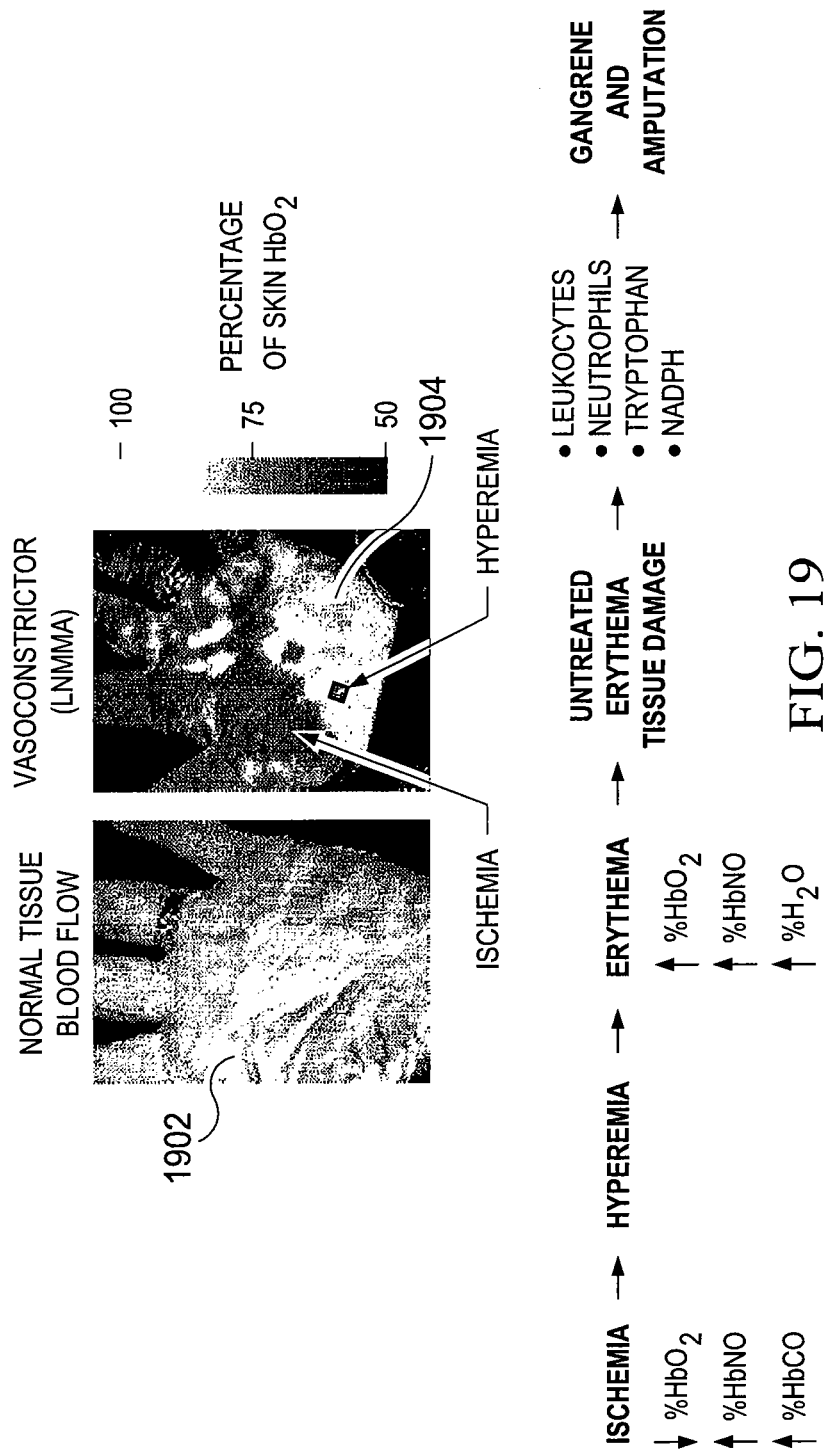

Upon admitting a patient to a medical facility or clinic, it is valuable to the hospital and clinicians to (1) detect, (2) classify and (3) predict (assess the risk of) a patient developing a medical malady, such as an ulcer, and (4) identifying the severity of the conditions, such as a burn and skin flaps. Various visual identifiers are subsequently described. For example, FIG. 19 is a pictorial representation of a hand being visualized to detect ischemia and hyperemia which may lead to an untreated condition, tissue damage, gangrene, or eventually even amputation. Image 1902 shows a hand with normal tissue and blood flow. Image 1904 shows a hand experiencing ischemia and hyperemia that may result from vasoconstriction.

Stage I ulcers may be identified visually by a blanchable redness similar to reactive hyperemia that does not subside after pressure is relieved. Hyperspectral imaging may visualize an increase in oxygenated hemoglobin, over time, a biomarker for Stage I ulcers.

A Stage III ulcer involves full thickness of the skin and may extend into the subcutaneous tissue layer. In some instances, there may be undermining damage making the wound much larger than it appears visually on the surface. Hyperspectral imaging may be useful in visualizing the wound margin below the surface of the skin based on the tissue chemistry measured by spectroscopic biomarkers.

Unstageable wounds may be vulnerable to several complications that may be detected and sorted using hyperspectral imaging. For example, gangrene is a result of infection or ischemia. Hyperspectral imaging may be used to visualize infections due to *staphylococcus, pseudomonas* and *e-coli* as well as other positive or negative bacterial strains. For ischemia, hyperspectral imaging may be used to map the location of an ulcer or a thrombus causing ischemia, aid in the revascularization by mapping the location of the microvasculature and larger blood vessels, and monitor perfusion during surgery. For example, the imaging system may be utilized to image tissue perfusion indicating a potentially redundant artery or an artery not perfusing a local area properly (e.g. kidney surgery). This system and process may be particularly valuable when performing micro vascular reconstruction surgery to attach a severed limb or during a face transplant. For example, the system may be utilized to look for proper tissue oxygenation, assess and predict the risk for post operative necrosis.

In addition, hyperspectral imaging may guide skin flap procedure in many ways. Preoperatively, hyperspectral imaging may be used to visualize the locations for perforators aiding the plastic surgeon in performing perforator flaps. During surgery hyperspectral imaging may be used to determine the best suture tension. The ideal suture tension ensures that the stitches hold the tissue in place but do not induce ischemia. The near to video rate chemically encoded images may be monitored to ensure flap perfusion is adequate during and after the procedure and ensuring the flap is viable to prevent flap failure. During skin flap procedures the hyperspectral imaging system may be utilized to look for perforator hyperfusion, flap perfusion, perfusion gradient, tissue viability, and potential necrosis.

In addition, imaging how close to the skin surface an ulcer has progressed may be a metric for determining the risk of the ulcer progressing and breaking the skin surface. Similarly, knowing the depth to which tissue has been burned may help assess a patient's treatment and the need for the patient to be admitted to the clinic. A possible system may include the depth information from optical coherence tomography (OCT), or using aperture dependant and con-focal methods combined with the chemical imaging of hyperspectral imaging.

Burns may be aided by hyperspectral imaging technology by providing chemically encoded images at near video rates to detect necrotic tissue and viability of the tissue. In addition, monitoring perfusion and viability of skin grafts, skin flaps, and suture tension may help the clinician increase positive outcomes and reduce hospital stays.

Hyperspectral imaging may provide chemical information from within and under the skin collected in vivo and non-invasively helping clinicians treat the dermatological ailments and visualize vascular changes. FIG. 20 shows another representation of hand visualization. For example, image 2002 may show unrestricted blood flow, image 2004 may show occluded ischemia, and image 2006 may show un-occluded hyperemia With reference to FIGS. 19 and 20, ulcers are most likely the result of improper blood perfusion (current hypothesis include ischemia and possibly reactive hyperemia effects) to an area of skin tissue. Ischemai and hyperemia may come about over time as a restrictive external pressure restricts the blood flow (ischemia) and when removed over perfuse (hyperemia) the tissue, which may damage the tissue if uncontrolled. Areas of ischemia and hyperemia may occur simultaneously in response to inhomogeneous vascular action or thrombosis as modeled pharmacologically with LNMMA. Ischemic conditions may be the result of an external mechanical pressure which may be a result of neuropathy. In other patients, a systemic ischemia due to a thrombosis or a high diastolic blood pressure may result in an ulcer that is local or counter lateral to the ischemia.

Hyperspectral imaging has a demonstrated ability for monitoring ischemia and reactive hyperemia in healthy human subjects that was modeled using a temporary restrictor as shown in FIG. 20. Hyperspectral imaging has measured a continuous deoxygenation of hemoglobin from basal levels during the restriction followed by an increased hemoglobin oxygenation above basal levels, reactive hyperemia, after removing the restriction. In healthy individuals a reactive hyperemia may return to normal basal tissue oxygenation levels. A patient with a stage I ulcer may be identified with Hyperspectral imaging as having a reactive hyperemia in an area of tissue surrounding by tissue at basal levels of tissue oxygenation.

Early detection of an ulcer may be visualized as an erythema in response to chronic hyperemia, a vasodilatation in response to the ischemia. Stage one ulcers may most likely be visualized to have an increase in the percentage of oxygenated hemoglobin and nitrosylated hemoglobin. Over time tissue may become damaged and inflamed which may see an influx of leukocytes, neutrophils, tryptophan, and NADPH that may be auto fluoresced. The illustrative embodiments may be utilized to predict and monitor ulcers using hyperspectral imaging by visualizing the presence and quantities of biomolecules which may include one or more of the following:

a. Increased % $HbO_2$ within the surface microvasculature
b. Increased % $HbO_2$ within the larger deeper vasculature
c. Increased % HbNO
d. Increased % $H_2O$
e. Bacterial & Fungal Infection
f. Leukocytes
g. Neutrophils
h. Tryptophan
i. NADPH Hyperspectral imaging may be useful in predicting an ulcer prior to its visual appearance using a combination of the above (a-d) optical spectroscopic biomarkers (diffuse reflectance spectra) and (e-h) auto-fluorophores (auto-fluorescence). The following are additional examples of detected components.

The system and method may be utilized to visualize the percentage of oxyhemoglobin ($HbO_2$), deoxyhemoglobin (Hb), and nitrosylated hemoglobin (HbNO) perfusing the microvasculature within millimeters of the skin. Microvascular occlusion and thresholds of tissue ischemia may be determined utilizing visible spectroscopy, such as wavelengths of 520-645 nm. Other known spectroscopic biomarkers that may be associated with the wound and within the visible spectral range are carboxy hemoglobin (HbCO) and methemoglobin (MetHb). Imaging may be performed for either individual levels of these inherent chromophors or a mathematical combination of chromophors associated with the condition.

The system and method may visualize the percentage of oxyhemoglobin perfusing the larger deeper blood vessels of the skin and determining thresholds of tissue ischemia at which tissue is damaged using NIR spectroscopy, such as 645-1000 nm. Other known spectroscopic biomarkers that may be associated with the wound and within the visible spectral range are $HbO_2$, Hb, Lipids, and water. Imaging may be performed individually or for a combination of chromophors associated with the selected condition.

The system and method may also monitor auto-fluorescence indicating the presence of an early immune response, for example inflammation, Leukocytes, Neutrophils, Tryptophan, NAD(P)H and may be an early detection and predictive (increased risk) for ulcer formation.

The illustrative embodiments utilize spectroscopy to detect various infections, such as fungal infections, bacterial infections, anthrax, pseudomonas, and aeruginosa. Imaging may also be performed for unknown spectroscopic biomarkers correlating with standard pathology and or histology. Advanced ulcers and wounds may be monitored for preventing and managing infection. Determining the depth at which the above biomarkers are within the tissue may be helpful in determining a risk factor for ulcer formation and classification.

Imaging the chemistry at different depths, layers or slices from the bone out toward the skin surface may help classify an ulcer and determine a risk factor for predicting an ulcer breaking the skin surface.

Currently there are there are wound characteristics during which negative pressure therapy (KCl Vac system) may not be the best treatment; however, there is controversy when and at what stage in a wound negative pressure therapy should be applied. Hyperspectral imaging may be helpful in identifying these characteristics and determining the ideal time and wound to which negative pressure therapy should be applied to reduce a wound healing time. Hyperspectral imaging may also be utilized to perform debridement and otherwise monitor tissue oxygenation.

Wounds: The illustrative embodiments image an absorbance spectrum or fluorescence of specific chromophers inherent to the skin in response to chemistry associated with a wound, such as ulcers, burns, etc. For example the imaging may be utilized to determine the degree of ischemia, inflammation, infection, necrotic tissue (that should be derided) and possibly a combination of biomarkers associated with these conditions, as described above and shown in FIGS. 19 and 20. The described systems and methods may be helpful in visualizing wound margins extending into the subcutaneous tissue layers, which on the surface may appear to be small, but affect much larger tissue areas in the deeper tissue layers. Ulcers, sores, pressure ulcers, bed sores, diabetic ulcers, lacerations, burns, and so forth are all considered wounds.

Skin Flaps: For stage III or IV ulcers most medical interventions include surgery or procedures, such as performing the tissue flap or free flap closure methods. Hyperspectral imaging may be useful in guiding the surgeon in assessing the wound and determining the best tissue flap or free flap closure method and ideal suture or stitching tension. For example, stitches that are too tight may induce an ischemia leading to the failure of the closure or impeding the healing process.

Post operatively using hyperspectral imaging may be used to identify risk factors for post operative skin flap failure and take appropriate actions. For example, actions may include loosening sutures that are too tight or become too loose due to fluid shifts between compartments or edema. Hyperspectral imaging may be utilized to monitor skin flap perfusion of $HbO_2$ and water during surgery and post operatively may help identify the best suture tension, and potential skin flap failure.

Pre-operatively hyperspectral imaging may be used to fluoresce indicators (ICG, Fluorescence and others) helping map the vasculature and lymphatics aiding a plastic surgeon. For example, HIS and ICG fluorescence may be utilized to help surgeons map lymphatics to determine ideal lymphatic-vein coupling. Pre-operative hyperspectral imaging may also be used to visualize the locations for perforators using chromophores inherent to the skin aiding the plastic surgeon in performing perforator flaps that are less bulky than traditional skin flaps and do not use muscle tissue. Pre-operative hyperspectral imaging may also be used to visualize and identify the anteriorly placed biliary structures of the gallbladder.

In another embodiment, vein viewing and tissue oxygenation technology may be used in adding surgeons during re-vascularization and skin flap procedures. Auto fluoresce of melanin when illuminated with ultra violet light be a noninvasive biomarker for visualizing melanoma, early detection, or tumor margins. Auto fluorescence of collagen may be a biomarker for imaging osteoporosis. Auto fluorescing collagen and NADPH may be a biomarker for uterine cervix cancerous lesions.

An enhanced hyperspectral imaging system may augment existing hyperspectral imaging technologies as herein described for enhancing clinical utility. Specific algorithms and various spectral analysis methods may be utilized to find spectral reference points outside of the spectral range of the chemistry being measured. In particular, FIG. 21 illustrates ray tracing incident light into tissue and visualizing the chemical nature of the tissue. The process may include: Ray tracing incident light (2101) into the tissue where the electron clouds of molecular constituents, Chromophores, (2102) absorb some of the wavelength energy changing the diffuse reflection spectrum of the light, the changes are detected (2103). Light can be reflected, diffusely reflected or absorbed by the tissue or tissue chromophores. Analyzing the diffuse reflection spectrum determines the chemistry (21044, 2105) within the tissue. Some chromophores known as fluorophores absorb light while emitting light at different wavelengths.

In one embodiment, a multi-functional imaging system or device may be switched (e.g. knob, switch, selector) between different modes of imaging, such as the spectral modes shown in FIGS. 17 and 18 as well as normal video. The system may include circuitry configured for analyzing tissue oxygenation and other tissue chemistry, vein viewing, blood flow, adaptive optics, and fluorescence imaging.

A disposable calibration standard and internal calibration method may be utilized for the illustrative embodiments. Combining methods, for example, vein viewing with tissue oxygenation produce a composite layered image that may be exploded or fused. For example, a normal color image may be overlaid with an image of tissue oxygenation (color encoded (quantified) at each image pixel) with a third layer of the venous anatomy further overlaid on top.

Hyperspectral imaging has a utility for visualizing the chemistry of the skin that may be used to determine the level of risk for developing an ulcer and monitoring wounds. Using preliminary data the skin may be imaged measuring the presence and levels of detect wounds prior to breaking the skin or the appearance of a visible indication or morphological change within the skin visible to the unaided trained clinician's eye.

A non-invasive, real time (near video rate), objective method classifying a wound and visualizing various states of the skin viable to eschar (dead tissue) may help clinicians determine the best treatment while managing the healing of the wound.

As shown by FIG. 13, n may be the number of wavelengths or spectrally dependent images. n may also represent the images that are collected and then processed with chemometrics producing a chemically encoded image or visualization. Subsequently, another 3-dimentional hypercube may be collected and processed at, near, or beyond video rates and over time these chemically encoded images may be assessed as a function of time also known as time resolved hyperspectral imaging.

The illustrative embodiments provide a method of performing hyperspectral imaging based on the chemical physics of optical spectroscopy, which is designed to be non-invasive, in vivo and remotely using the described systems and technology capable of near video rate chemically encoded images.

In one embodiment, between illuminating the site with particular spectrums of light, a light source may trace out or illuminate the site with reference points or indicators for a surgeon, clinician, or other individual analyzing the site. For example, necrotic tissue sections may be specifically called out automatically. In one embodiment, particular color spectrums may give preferable results for analyzing the site. As a result, additional filtering and complex processing may not be required for the acquired images. Reduced complexity means that the size of the system and the processing system may be reduced significantly. In addition, the desired characteristics/chemicals associated with the individual spectra may be obtained more quickly. For example, oxygenation of hemoglobin may be determined utilizing the disclosed spectra. In one embodiment, LEDs may be configured to provide the desired spectra. In another embodiment, optics and filtering may be utilized as adaptive methods for the hyperspectral imaging herein described. For example, structured light may be utilized to minimize scattering and increasing imaging at greater tissue depths or to determine the volume of a wound. In addition structured light may be utilized to correct curvature effect and flatten out the surface up to 30 degrees in curvature.

Figure 22:
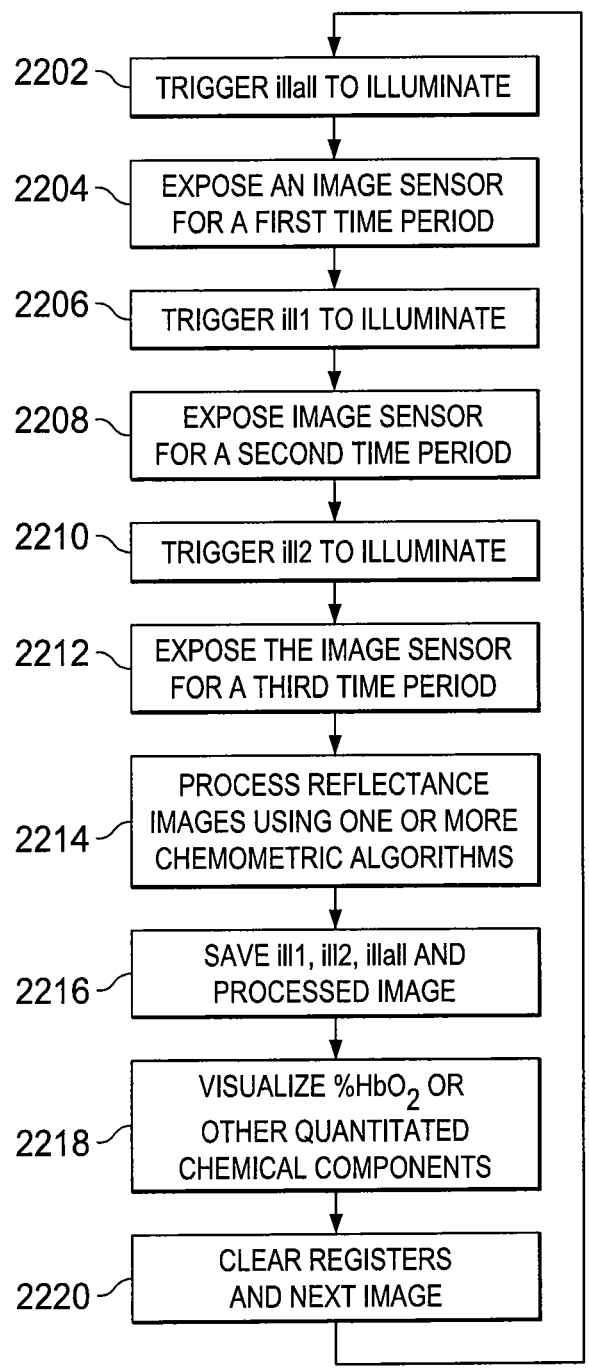
FIG. 22 is a flowchart of a process for multiple illuminations in accordance with an illustrative embodiment.

FIG. 22 is a flowchart of a process for multiple illuminations in accordance with an illustrative embodiment. The process of FIG. 22 may be implemented by an imaging and illumination system as are herein described. The exposure times may all be the same, but for improved signal-to-noise ratio the imaging sensor or detector may be exposed in a ratio of 3.87:1.95:1 relative to ill1, ill2, and illall (e.g. first, second, and third time periods) to reduce the signal-to-nose ratio. However, any number of ratios may also be utilized. The illustrative embodiments, are unique in distributing the chemometrics in the complex or spectral illumination along with the algorithmic processing. Many existing solutions are performed utilizing only algorithms and not synchronized illuminations utilizing specified spectra.

The process may begin by triggering illall to illuminate (step 2202). Next, the system exposes an image sensor for a first time period (step 2204). Next, the system trigger ill1 to illuminate (step 2206). Next, the system exposes an image sensor for a second time period (step 2208). Next, the system triggers ill2 to illuminate (step 2210). The system exposes the image sensor for a third time period (step 2212). Next, the system processes reflectance images using one or more chemometric algorithm (step 2214). Next, the system saves ill1, ill2, illall and the processed images (step 2216). The system visualizes % $HBO_2$ or other quantitated chemical components (step 2218). As previously described any number of chemical components may be utilized. Next, the system clears registers and moves onto a next image (step 2220). The next images may be acquired and processed at or greater than video rates.

The illumination order of ill1, ill2, and illall may vary in various embodiments. Other embodiments may utilize varying orders for enhancing data acquisition. For example, only one illumination may be utilized using the previous two images to determine the visualization.

Figure 23:
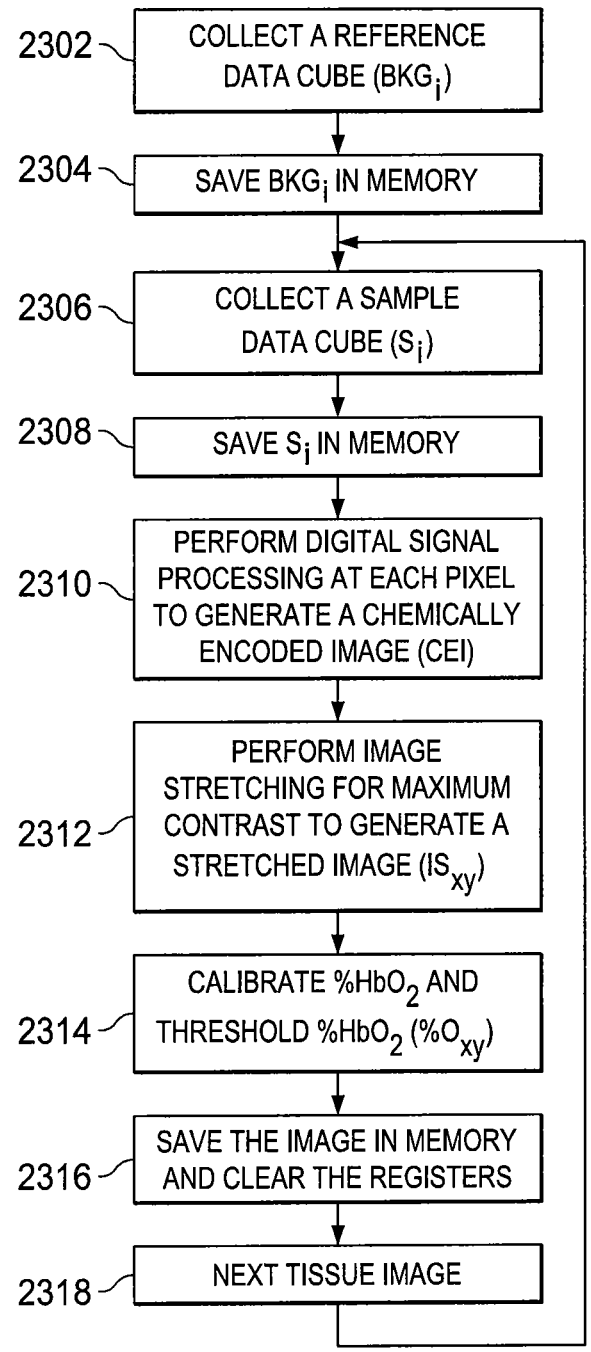
FIG. 23 is a flowchart of a process for data collection in accordance with an illustrative embodiment.

FIG. 23 is a flowchart of a process for data collection in accordance with an illustrative embodiment. In one embodiment, the process of FIG. 23 may further describe step 2214 of FIG. 22. The process of FIG. 23 may begin by collecting a reference data cube ($BKG_i$) (step 2302). Collecting the reference data cube may have been previously performed as embodied by steps 2202-2212 of FIG. 22.

Next, the system saves $BKG_i$ in memory (step 2304). In one embodiment, the reference data cube or background (BKG) may be defined by illuminating the field of view using ill1, ill2, illall where there is a 100% referenced standard. For example, Spectralon may be imaged with the field of view ($BKG_1$=ill1, $BKG_2$=ill2, $BKG_3$=illall).

Next, the system collects a sample data cube ($S_i$) (step 2306). The sample data cube may be defined as illuminating the field of view using ill1, ill2, illall, when the tissue, organ, or target is within the target area or field of view.

The system save $S_i$ in memory (step 2308). For example, steps 2202-2212 of FIG. 22 may be performed. The system performs digital signal processing at each pixel to generate a chemically encoded image (CEI) (step 2310). In one embodiment, the chemically encoded image may be represented by $CEI_{xy}=((\log_{10}(BKG_{1xy}/S_{1xy})))/(((\log_{10}(BKG_{3xy}/S_{3xy})))-((\log_{10}(BKG_{2xy}/S_{2xy})))/(((\log_{10}(BKG_{3xy}/S_{3xy}))))$. In one embodiment, a normal image may be overlaid with a hyperspectral image and one mapping the vasculature of lymphatics that have been injected with ICG. The pixels may be registered spacially, encoded for display, or otherwise processed. In addition, larger fields of view may be stitched together.

Next, the system performs image stretching for maximum contrast to generate a stretched image $IS_{xy}$ (step 2312). The image stretching may be utilized to maximize contrast for varying melanin contents. In one embodiment, fl and ul are approximately −0.2 and 0.3 for light skin tones (respectively) and −0.25 and +0.25 for darker tones. In addition, a feedback loop may be utilized to converge to a value by determining the best image stretching constants relative to varying levels of melanin. In one embodiment the stretched image may be represented by $IS_{xy}=(unit8((CEI_{xy}-fl)*255)./(ul-fl)$.

The system calibrates % $HbO_2$ calibration and thresholds % $HbO_2$ (% $O_{xy}$) (step 2314). Step 2314 may be performed for each pixel of the image. In one embodiment, the % $O_{xy}=(IS_{xy}/255)*80+10$. A variety of thresholds may be utilized to assess diseases (as are herein described). For example, in skin flap procedures clinical data indicates a 60±% $HbO_2$ indicates the tissue is at risk of becoming necrotic post-operatively. Other examples of thresholds may include predicting the viability of kidney tissue and post operative stroke.

Next, the system saves the image in memory and clears the registers (step 2316). The system then moves onto the next tissue image (step 2318).

Figure 24:
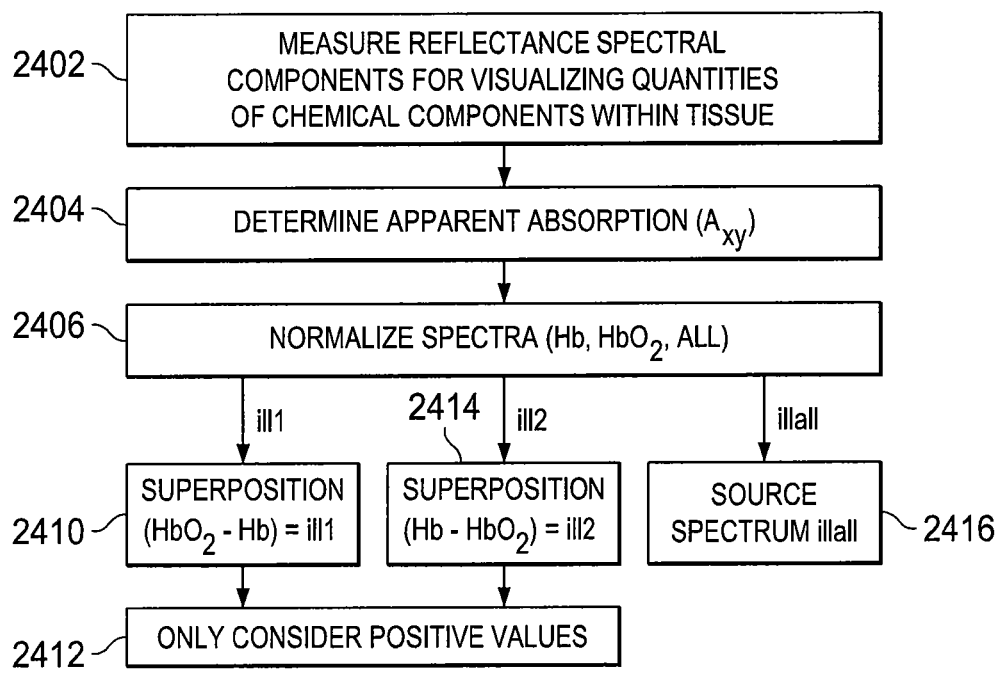
FIG. 24 is a flowchart of a process for chemometric illuminations in accordance with an illustrative embodiment.

FIG. 24 is a flowchart of a process for chemometric illuminations in accordance with an illustrative embodiment. The process of FIG. 24 may begin by measuring reflectance spectral components for visualizing quantities of chemical components within tissue (step 2402). The chemical components, may include, but are not limited to % $HbO_2$.

Next, the system determines apparent absorption ($A_{xy}$) (step 2404). $A_{xy}(\lambda_i)=Log(R_{xy}(\lambda_i)_o/R_{xy}(\lambda_i))$. Next, the system normalizes the spectra (Hb, $HbO_2$, all). In one embodiment, $(\lambda_i-Max(\lambda_{i-j}))/(Max(\lambda_{i-j})-Min(\lambda_{i-j}))$. The system performs superposition ($HbO_2$−Hb)=ill1 (step 2410). The system only considers positive values (step 2412). The system also performs superposition (Hb−$HbO_2$)=ill2 (step 2414) and once again only considers positive values (step 2412). The system also utilizes source spectrum illall (step 2416).

Figure 25:
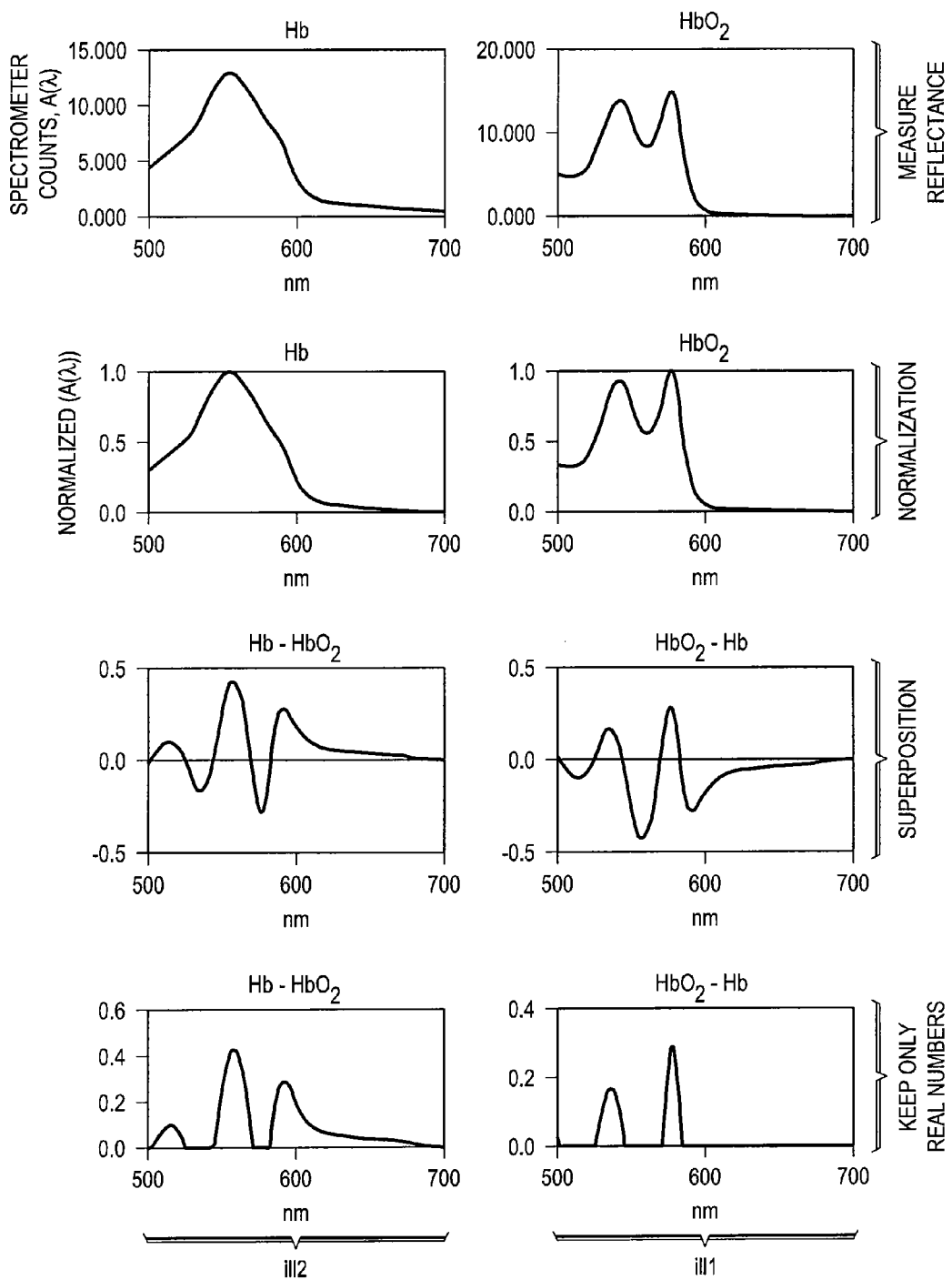
FIG. 25 is a representation of chemometric illuminations in accordance with an illustrative embodiment.

FIG. 25 is a representation of chemometric illuminations in accordance with an illustrative embodiment. The graphs of FIG. 25 are associated with the measured reflectance, normalization, superposition, and real number values determined or measured during the processes of FIGS. 22-24. In addition, the illumination profile of the source for illall may be all LEDs illuminated. For a lamp based system, illall would be the lamp. For the OL490 DMD system illall may be all mirrors on.

In another embodiment, imaging system may also be utilized for large field or narrow field treatments. For example, the imaging system may be utlilized to perform phototherapy, such as location-based sterilization for a wound, and spectra-based treatments for conditions, such as rosatia. For example, UV may be utilized to expose an area simulating a tan for cosmetic purposes.

The previous detailed description is of a small number of embodiments for implementing the invention and is not intended to be limiting in scope. The following claims set forth a number of the embodiments of the invention disclosed with greater particularity.

What is claimed:

1. A method for visualizing a biological sample, the method comprising:
   selecting a first, second and third spectra for illuminating the biological sample to indicate one or more chemicals in the biological sample, wherein the third spectrum is a summation of the first and second spectra;
   successively illuminating the biological sample with the first, second and third spectra;
   analyzing reflected light from the first, second and third spectra to determine characteristics of the biological sample.

2. The method of claim 1, wherein the method is controlled remotely.

3. The method of claim 1, wherein the first, second and third spectra include wavelengths from ultraviolet to thermal.

4. The method of claim 1, wherein the illuminating is performed a plurality of times utilizing a plurality of spectra, wherein the plurality of spectra are complex spectra.

5. The method of claim 1, wherein the first, second and third spectra are generated by light emitting diodes.

6. The method of claim 1, wherein the reflected light is used for visualizing Hb and $HbO_2$.

7. The method of claim 1, wherein the analyzing comprises:
   acquiring one or more images for each of the first, second and third spectra.

8. The method of claim 7, wherein the one or more images are utilized to generate an imaging cube.

9. The method of claim 1 further comprising:
   illuminating the biological sample with the first spectrum to obtain a second reflected light from the first spectrum; and,
   analyzing reflected light from the second and third spectra and the second reflected light from the first spectrum to determine characteristics of the biological sample.

10. The method of claim 1 further comprising:
    illuminating the biological sample with the second spectrum to obtain a second reflected light from the second spectrum; and,
    analyzing reflected light from the first and third spectra and the second reflected light from the second spectrum to determine characteristics of the biological sample.

11. The method of claim 1 further comprising:
    illuminating the biological sample with the third spectrum to obtain a second reflected light from the third spectrum; and,
    analyzing reflected light from the first and second spectra and the second reflected light from the third spectrum to determine characteristics of the biological sample.

12. A system for performing hyperspectral imaging, the system comprising:
    a hyperspectral illuminator configured to illuminate a target utilizing a plurality of spectra;
    a camera in communication with the hyperspectral illuminator and configured to capture one or more images for each of the plurality of spectra;
    a data processing system controlling the hyperspectral illuminator and the camera, the data processing system processes data captured by the camera, the data processing system triggers illumination of the target for each of the plurality of spectra, the data processing system controls exposure of the camera for each of the plurality of spectra and at least one exposure is a different time period.

13. The system according to claim 12, wherein the plurality of spectra are complex spectra.

14. The system according to claim 12, wherein the plurality of spectra are three spectra generated by light emitting diodes.

15. The system according to claim 12, wherein the one or more spectra include wavelengths of 270-1000 nm.

16. The system according to claim 12, wherein reflectance and absorption are determined for each of the one or more images to determine whether one or more thresholds are exceeded for the target.

17. A method for performing imaging, comprising:
    illuminating a target with a plurality of spectra;
    exposing an image sensor of an imaging system for one of a plurality of time periods associated with each of the plurality of spectra, wherein at least one time period is a different length;
    processing reflectance images from the target utilizing chemometric algorithms; and
    visualizing one or more chemicals in the target.

18. The method of claim 17, wherein at least one of the reflectance images comprises hyperspectral fluorescence.

19. The method of claim 17, wherein the target is exposed for a different time period for at least one of the plurality of spectra.

20. The method according to claim 17, further comprising:
    saving the reflectance images.

21. The method according to claim 17, further comprising:
    performing digital signal processing for the reflected images; and
    performing image stretching.

22. The method according to claim 17, further comprising:
    measuring reflectance components for the one or more chemicals;
    determining apparent absorption;
    normalizing the plurality of spectra; and
    performing superposition of the plurality of spectra.

23. The method according to claim 17 wherein the step of visualizing comprises encoding an image of the target based on the step of processing reflectance images to produce an encoded image, and the encoded image comprises a plurality of image pixels selected from the group consisting of: a plurality of color pixels; and, a plurality of gray-scale pixels.

* * * * *